United States Patent [19]
Dedolph

[11] Patent Number: 5,556,765
[45] Date of Patent: Sep. 17, 1996

[54] REACTOR USING TUBULAR SPIROIDS FOR GAS/LIQUID PROPULSION

[76] Inventor: Richard R. Dedolph, 22W510 71st. St., Naperville, Ill. 60540

[21] Appl. No.: 199,385

[22] Filed: Feb. 18, 1994

[51] Int. Cl.[6] .............. B01F 9/02; B01J 10/02; C12M 1/10; C12M 3/04
[52] U.S. Cl. .................. 435/41; 138/DIG. 11; 366/135; 366/155.1; 366/196; 366/227; 422/209; 422/227; 422/229; 422/312; 435/286.5; 435/289.1; 435/293.2
[58] Field of Search .................. 138/177, DIG. 8, 138/DIG. 11; 422/209, 227, 229, 312; 435/303, 312, 285, 286, 41; 210/150, 151; 366/135, 155, 196, 227, 155.1

[56] References Cited

U.S. PATENT DOCUMENTS

| | | | |
|---|---|---|---|
| Re. 24,822 | 5/1960 | Pallotta et al. | 47/1.4 |
| 157,191 | 11/1874 | Cameron | 417/94 |
| 199,450 | 1/1878 | Kirkham et al. | 261/92 |
| 254,003 | 2/1882 | Gontard | 159/12 |
| 389,071 | 9/1888 | Glessner | 417/137 |
| 631,002 | 8/1899 | Van Vriesland | 261/28 |
| 773,316 | 10/1904 | Evans | 417/94 |
| 896,581 | 8/1908 | Robinson et al. | 417/94 |
| 1,021,714 | 3/1912 | Bramanti-Mattei et al. | 417/94 |
| 1,102,222 | 6/1914 | Abbott, Jr. | 417/68 |
| 1,114,603 | 10/1914 | Giger | 417/137 |
| 1,134,432 | 4/1915 | Aylsworth | 95/219 |
| 1,395,267 | 11/1921 | Fisher | 415/73 |
| 1,720,999 | 7/1929 | Cawley | 416/177 |
| 1,912,480 | 6/1933 | Houlis | 261/92 |
| 1,995,791 | 3/1935 | Bonnot | 138/177 |
| 2,106,025 | 1/1938 | Faber | 261/92 |
| 2,543,242 | 2/1951 | Kent et al. | 494/60 |
| 2,544,154 | 3/1951 | Hampton | 415/73 |
| 2,586,692 | 2/1952 | Morel | 261/92 |
| 2,715,795 | 8/1955 | Pallotta et al. | 47/1.4 |
| 3,098,602 | 7/1963 | Torluemke | 417/199.1 |
| 3,266,555 | 8/1966 | Thier | 417/199.1 |
| 3,335,081 | 8/1967 | El-Naggar | 210/150 |
| 3,489,074 | 1/1970 | Farkas et al. | 99/360 |
| 3,565,797 | 2/1971 | Gresham | 210/602 |
| 3,613,890 | 10/1971 | Hellqvist | 210/150 |
| 3,647,081 | 3/1972 | Engelbart | 210/150 |
| 3,812,016 | 5/1974 | Muller | 435/285 |
| 3,875,058 | 4/1975 | Nordgard | 210/151 |
| 3,985,653 | 10/1976 | Ahlgren | 210/150 |
| 4,009,734 | 3/1977 | Sullivan | 138/177 |
| 4,010,102 | 3/1977 | Jarvstrat | 210/151 |
| 4,010,647 | 3/1977 | Kisseil et al. | 73/864.34 |
| 4,022,689 | 5/1977 | Kato et al. | 210/151 |
| 4,065,279 | 12/1977 | McCullough | 62/510 |
| 4,082,484 | 4/1978 | McCullough | 418/55.2 |
| 4,188,786 | 2/1980 | Franch | 60/325 |
| 4,245,949 | 1/1981 | Candler | 415/73 |
| 4,267,051 | 5/1981 | Uhlmann | 210/619 |
| 4,310,630 | 1/1982 | Girard et al. | 435/284 |
| 4,351,721 | 9/1982 | Frandsen | 210/150 |
| 4,540,491 | 9/1985 | Zimmer | 210/619 |
| 4,676,892 | 6/1987 | Grabowski | 210/150 |
| 4,897,356 | 1/1990 | Simpson et al. | 435/262 |
| 4,990,075 | 2/1991 | Wogoman | 422/58 |
| 5,002,659 | 3/1991 | Bidenko et al. | 210/150 |

FOREIGN PATENT DOCUMENTS

| | | | |
|---|---|---|---|
| 2493337 | 5/1982 | France | 435/312 |
| 553368 | 12/1956 | Italy . | |

OTHER PUBLICATIONS

Translation of French Patent 2,493,337 (May 7, 1982).

*Primary Examiner*—Jeffrey E. Russel
*Attorney, Agent, or Firm*—Wood, Phillips, VanSanten, Clark & Mortimer

[57] ABSTRACT

A reactor includes a reaction vessel that defines a reaction chamber. Completely or partially within the reaction chamber is at least one spiroid. The spiroid is operably associated with the reaction vessel so that rotation of the reaction vessel causes the spiroid to rotate and liquid to be transferred through the spiroid. The spiroid can circulate gas and liquid within the reaction chamber, introduce fresh gas and liquid into the reaction chamber or discharge gas and liquid from the reaction chamber.

47 Claims, 13 Drawing Sheets

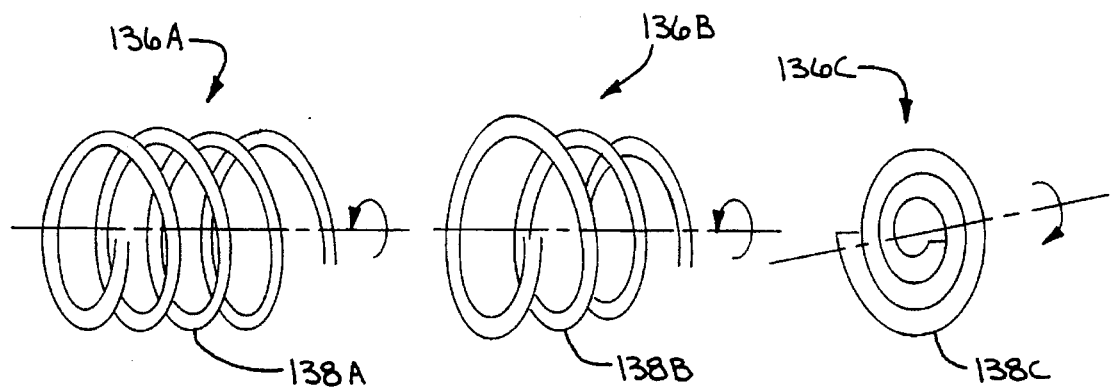
FIG. 5A  FIG. 5B  FIG. 5C
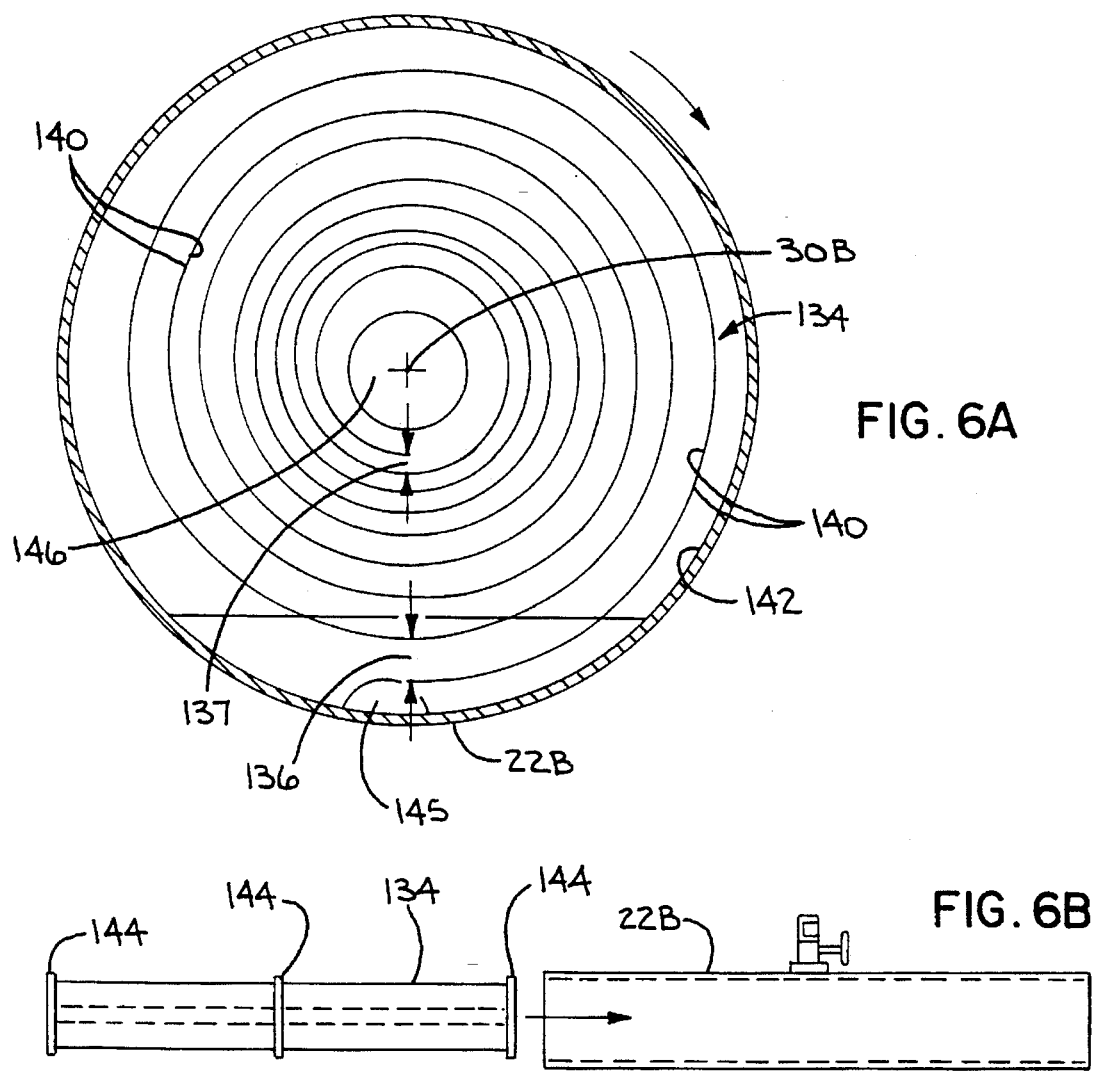
FIG. 6A
FIG. 6B

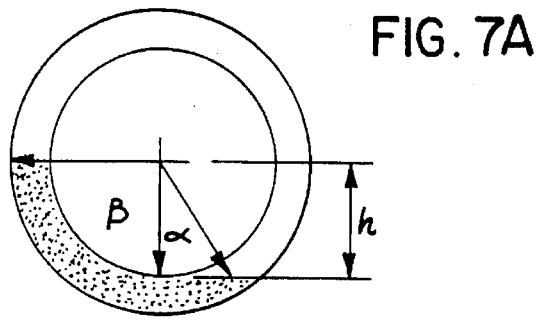
A. HEAD GENERATED WITH MINIMAL LIQUID PISTON DISPLACEMENT
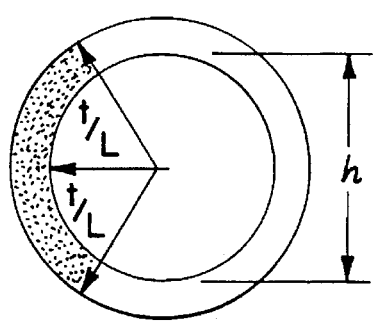
B. HEAD GENERATED WITH MAXIMUM LIQUID PISTON DISPLACEMENT
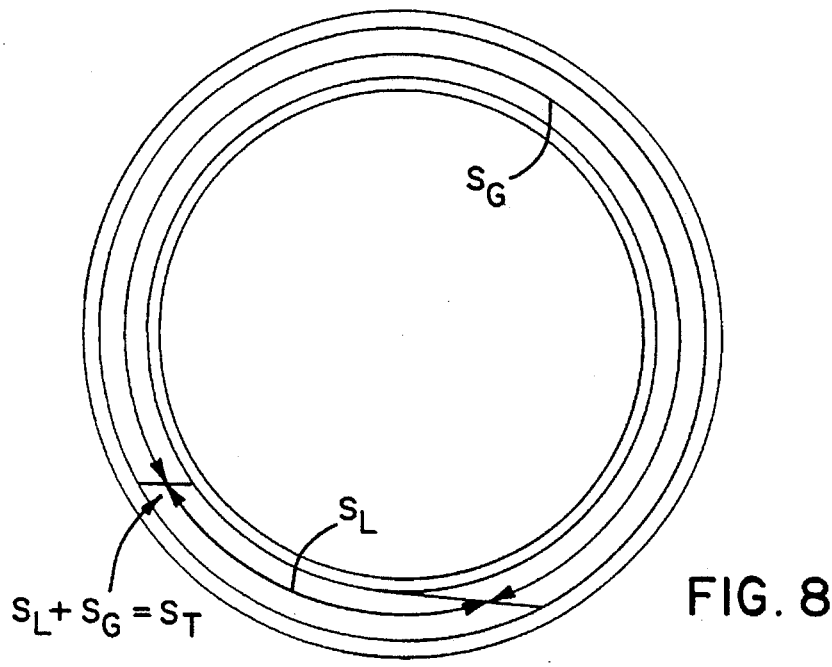
FIG. 8

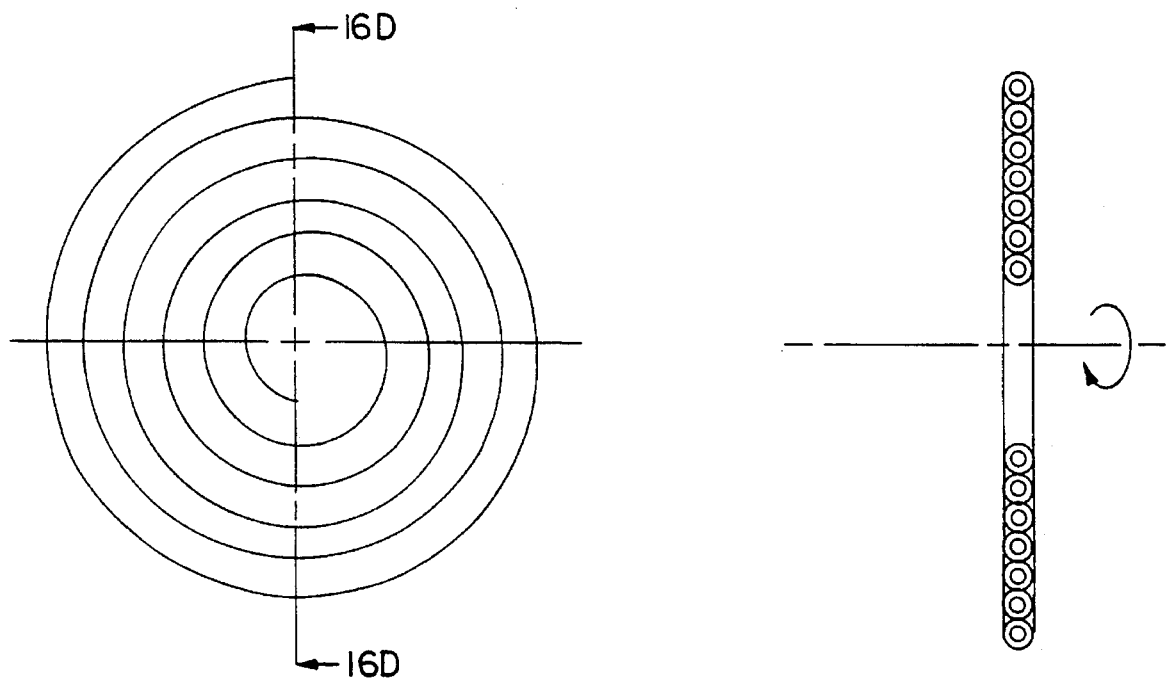
FIG. 16D
FIG. 16A
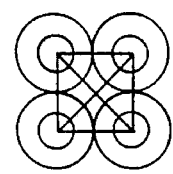
FIG. 16B
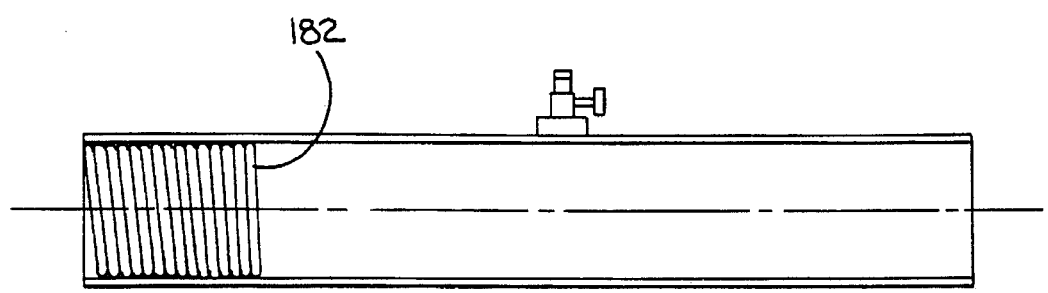
FIG. 16C

REACTOR USING TUBULAR SPIROIDS FOR GAS/LIQUID PROPULSION

TECHNICAL FIELD

This invention generally relates to a reactor that includes at least one spiroid. The spiroid can recirculate the contents of the reactor or can be used to introduce additional components into the reactor. More particularly, the invention relates to a bioreactor for the culture of cells or tissues that use a spiroid to recirculate the contents of the bioreactor, introduce gas, liquid and/or solid phases into the bioreactor and/or remove the contents from the bioreactor.

BACKGROUND OF THE INVENTION

Reactors are used in research and industry to position and maintain gas, liquid and/or solid phases contained therein in contact with each other to effect a reaction. Mixing is often required to obtain the desired amount of contact. Polymerization is one reaction that can be performed. Another reaction is a bioreaction wherein organisms, e.g., cells, are cultured to produce additional cells or a product of the cells. Reactors in which bioreactions are performed are called bioreactors or fermentors. The reactants include the cells and the gas, liquid or solid phases. Bioreactors will be discussed hereinafter, it being understood that similar problems exist with other reactors.

Bioreactors include laboratory (small) scale bioreactors, e.g., stationary shaker and roller bottles, stirred tank, airlift, membrane and rotating drum types. Large scale bioreactors are usually of the stirred tank type, occasionally of the rotating drum type and rarely of the bubble column and airlift type.

Some cell cultures are grown suspended in the liquid phase while others must be attached to a surface (attachment dependent cells) within the bioreactor to be grown. The cells obtain nutrients contained in the gas, liquid or solid phase from direct contact. A uniform and optimal nutrient level throughout the bioreactor is necessary to maximize cell growth and propagation. Adequate mixing contributes to a uniform nutrient level. Other bioreactors have shortcomings that inhibit obtaining a uniform and optimal nutrient level.

Roller bottle, bubble column and airlift bioreactors only provide mixing in one direction and can result in a nonuniform nutrient level. When fresh nutrient-containing gas, solid or liquid phases (medium) are added, they may not be evenly dispersed within the bioreactor or may take an extended time period to be uniformly dispersed. Thus, some of the cells can be exposed to a non-optimal nutrient levels. These problems are exacerbated as the cells grow and propagate which increases the viscosity of the liquid phase and makes mixing and obtaining a uniform and optimal nutrient level more difficult.

Impellers used to effect mixing can damage the cells due to impact of the impeller upon the cells. Damaging of cells is of course contrary to the purpose of the bioreactor. As the cells multiply in suspended culture, they increase the viscosity of the liquid phase which increases the number of cells damaged by the impeller.

Bioreactors that do not permit the gas, liquid and/or solid phases to be removed therefrom or introduced thereto cannot maintain the optimum nutrient level because the cells consume nutrients and change the nutrient level within the bioreactor. Superoptimal levels can be used initially but the optimum levels are only achieved for a short time period and soon suboptimal levels occur. The nutritional requirements of cells change as they go through different stages of growth. A bioreactor that cannot respond to these changes by changing the gas, liquid or solid phases as required cannot maximize cell growth and propagation.

The bioreactor can be opened, spent gas, liquid or solid phases removed therefrom and fresh medium introduced thereto in order to change the nutrient levels. However, opening of the bioreactor is undesirable because sterility must be maintained therein and opening the bioreactor increases the risk that sterility will not be maintained.

Some bioreactors use peristaltic or some other type of pump to introduce and remove gas, liquid or solid phases. When cells are suspended in the liquid phase the pump can damage the cells that pass through the pump. Damaging the cells is contrary to the goal of the bioreactor.

It sometimes is necessary to test the contents of the bioreactor to determine the developmental stage of the cells, the nutritional level, gas level or the like within the bioreactor. Many bioreactors, e.g., roller bottles, do not provide a mechanism for sampling while the bioreactor is operating. Roller drums may provide for sampling but not without an external pump which, as discussed above, can damage the cells.

The surface area of many bioreactors is limited which limits the number of cells that can be attached thereto. Often, a large number of roller bottles are used to culture attachment dependent cells. The number of cells per roller bottle is limited by the surface area of the interior of the roller bottle, not by its volume.

A reactor that does not exhibit the aforementioned shortcoming of the existing reactors is highly desirable.

SUMMARY OF THE INVENTION

The invention is directed to a reactor that provides mixing of the reactants, e.g., gas, liquid and solid phases (which are sometimes collectively and individually referred to as medium) and organisms, contained therein and permits the removal and introduction of reactants in a controlled manner to maintain optimal levels of the reactants. In particular, the invention provides a bioreactor for cell or tissue propagation, growth and maintenance that provides mixing without damaging the cells and permits controlled removal and introduction of gas and liquid to maintain optimal nutrient levels for maximizing cell growth and metabolism. Further, the bioreactor provides for high rates of gas absorption by the liquid. The invention will be described in terms of a bioreactor, it being understood that the invention is also of other types of reactors. Cells will be used as a representative organism that can be grown and propagated in the reactor, it being understood that all types of cells and tissues, both animal and plant, can be grown and propagated in this bioreactor.

According to the invention, the bioreactor includes a rotatable reaction vessel that defines a reaction chamber therein that is capable of holding liquid and gas phases. A tubular spiroid is operably associated with the bioreactor so that rotation of the bioreactor causes rotation of the spiroid and transport of liquid and gas phases through the spiroid lumen. The spiroid has an inlet, and generally has at least one coil, but in some applications may be comprised of a partial coil, and an outlet. The spiroid can be a recirculation spiroid located entirely or partially within the reaction chamber to recirculate liquid within the reaction chamber.

Alternatively, the inlet can be located exteriorly of the reaction chamber and the outlet can be located within the reaction chamber so that liquid and gaseous phases or the liquid phase alone may be continuously metered into the reaction chamber by the spiroid. In a further alternative, the inlet of the spiroid is located within the reaction chamber and the outlet is located exteriorly of the reaction chamber so that rotation causes the liquid phase and introduced gas phase to be transferred from the reaction chamber to the exterior of the reaction chamber while maintaining the medium level and gas pressure in the reactor chamber constant.

Preferably, the reaction vessel is cylindrical and defines a cylindrical reaction chamber with the axis of rotation being perpendicular to the cross section of the reaction chamber. Thus, the shear forces the cells or tissues experience during rotation due to movement of the interior walls of the reaction vessel with respect to the liquid are minimal and little or no damage is caused to the cells. Rotation as such causes radial mixing that is mixing of the liquid in planes normal to the axis of rotation of the reaction vessel.

The spiroid is preferably made of smooth bore tubing. Organisms can be transferred through the lumen of such tubing with a minimal amount of shear force and little or no damage to them. When both the inlet and outlet of a recirculation spiroid are within the reaction chamber, they can be positioned to recirculate gas and liquid phases along the length of the reaction chamber. Thus, mixing not only occurs normal to this axis of rotation but also along the length of the chamber. This dual mixing maintains uniform nutrient and gas composition within the bioreactor.

Fresh nutrients in the gas and liquid phases (medium) can be introduced into the reaction chamber using an introduction spiroid whose inlet is exteriorly located and whose outlet is located within the reaction chamber. The inlet can be in a reservoir vessel that is sealed to the environment and contains the gas and liquid phases. Thus, the optimal nutritional and gas levels can be maintained within the reaction chamber while maintaining sterility therein. The speed of rotation of the reaction vessel and the liquid level in the fresh medium reservoir vessel can be adjusted to control the rate of fresh medium introduction.

Gas and liquid phases can be removed from the reaction chamber when the inlet of a sampling spiroid is within the reaction chamber and the outlet is located exteriorly of the reaction chamber.

The contents of the bioreactor can be sampled by having a section of the recirculation spiroid extending to the exterior of the reaction vessel. This configuration enables sampling to determine the developmental stage of the cells, the nutritional level, and the like while the sealed bioreactor is operating and while maintaining sterility.

Spiroidal inserts can be placed within the reaction chamber to increase the surface area of the reaction chamber. Such a spiroid permits nutrients to flow past the cells with minimal shear force to inhibit cell damage. The insert spiroid can be designed so that the flow rate across its surface is substantially constant, controllable and equivalent to the flow rate over the walls of the vessel.

The spiroids employed necessarily transport both gas and liquid phases during each rotation. To achieve this, a liquid plug must be formed within the tubular spiroid lumen. The liquid plug is formed by selecting a depth of immersion in the liquid phase for the inlet of the spiroid to take up enough liquid to seal the lumen during each rotation. To so seal the spiroid the liquid plug must have a cross-sectional area equal to that of the lumen. If the spiroid has a number of coils whose diameters progressively and appropriately decrease from the coil having the inlet to the outlet coil a balance between hydrostatic and pneumatic pressures may be achieved with a low per rotation liquid delivery rate. This is particularly important when the spiroid has a lumen that is greater than about one inch.

Numerous other advantages and features of the present invention will become readily apparent from the following detailed description of the preferred embodiments, the drawings and the appended claims.

BRIEF DESCRIPTION OF THE DRAWINGS

FIG. 5A to 5C schematically illustrate the shapes of various spiroids.

FIGS. 6A and B are depictions of an insert spiroid for growth of an attachment dependant culture.

FIGS. 7A and B are diagrams showing the effect of displacement of a water piston in a coil upon the hydrostatic head which may be derived from it.

FIG. 8 is a diagram of the relationship of the liquid gas and total volume in the coil of a spiroid.

FIG. 16A–D is a diagrammatic representation of a uniform bore tubular spiral suitable for use as a reaction chamber insert.

DETAILED DESCRIPTION OF THE PREFERRED EMBODIMENTS

This invention is susceptible to embodiments in many different forms. Described in detail herein, are presently preferred embodiments of the invention. It should be understood that the present disclosure is to be considered as an exemplification of the principles of this invention and is not intended to limit the invention to the specific embodiments described.

The present invention is of a reactor suitable for maintaining and mixing reactants, e.g., organisms and nutrients contained in a solid, liquid or gaseous phase (which can be referred to individually or collectively as medium), in an environment that facilitates the reaction. The solid phase can be suspended or dissolved in, or otherwise transported by, the liquid phase. The reactor can be used for performing reactions such as the culture of cells, tissues, polymerization, catalysis and the like and has a myriad of other applications in chemistry and biochemistry as well as biotechnology.

Figure 1:
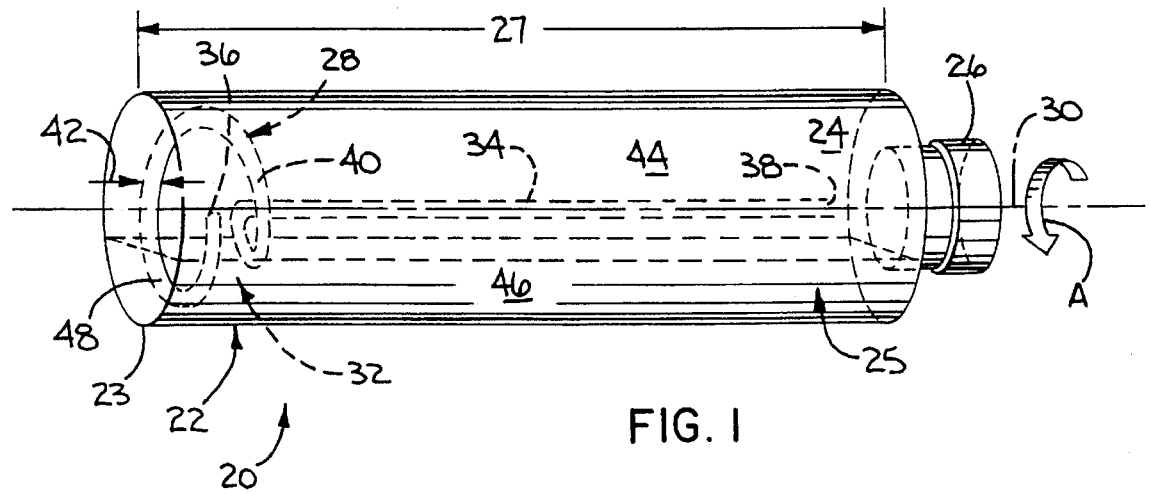
FIG. 1 is a partially broken away view of a basic reactor of the present invention using an internal recirculation spiroid.

The reactor 20 of FIG. 1 includes an elongate reaction vessel 22 that defines an elongate reaction chamber 24 therein. Preferably, the reaction vessel 22 is cylindrical having a round cross section perpendicular to the axis of rotation 30, although other shapes may be utilized. The reaction chamber 24 has a proximal end 23, a distal end 25 and a length 27. A removable cap 26 permits access to the reaction chamber 24. Entirely within the reaction chamber 24 is a recirculation spiroid 28. The spiroid 28 has a coil 32 in fluid communication with an elongate recirculation element 34, an inlet 36 on the coil 32, an outlet 38 on the recirculation element 34 spaced from the coil 32, a lumen 40 that extends the length of the spiroid 28 and that has a cross-sectional diameter 42 that is preferably uniform throughout the length of the spiroid 28. The elongate recirculation element 34 is parallel to an axis of rotation 30 for the reaction vessel 22. Rotation of the reaction vessel 22 about an axis 30 in the direction indicated by arrow A causes the spiroid 28 to similarly rotate.

In operation, the cap 26 is removed and gas phase 44 and liquid phase 46 are introduced into the reaction chamber 24 and it is recapped. It being understood that the gas phase 44 can be a reactant or an inert gas phase and that the liquid phase 46 can be an admixture of reactants. FIG. 1 illustrates the level of the liquid phase 46 as being below the elongate recirculation element 34. However, the level of the liquid phase 46 can be above the elongate recirculation element 34.

The reaction vessel 22 is rotated which rotates the spiroid 28. Preferably, the inlet 36 is immersed in the liquid phase 46 to a depth that forms a liquid piston 48 that extends across the diameter 42 and seals the lumen 40 trapping the gas phase already in the lumen 40. Continued rotation of the reaction vessel 22 causes the gas phase 44 to enter the lumen 40 through the inlet 36 and the liquid piston 48 to move along the lumen 40 within the coil 32 pushing gas phase that is already within the lumen 40 forward. When the inlet 36 reenters the liquid phase 46, the liquid piston 48 enters the elongate recirculation element 34 and the gas and liquid phases are discharged through the outlet 38 into the gas 44 and liquid phases 46. The liquid piston 48 is reformed during each rotation and traps the gas phase that had entered the lumen 40 during the previous rotation. Continued rotation of the reaction vessel 22 continues the process of the formation of a liquid piston 48 that traps gas phase in the lumen 40, the liquid piston 48 moving through the lumen 40 and pushing the gas phase in front of it until the trapped gas phase and the liquid piston 48 enter the elongate recirculation element 34 and flow back into the gas phase 44 and the liquid phase 46. When the level of the liquid phase 46 is above the elongate recirculation element 34 (not shown), the gas phase transferred by the spiroid 28 exits from the outlet 38 and bubbles up through the liquid phase 46 increasing gas dissolution.

Rotation of the reaction vessel 22 causes the liquid phase 46 to enter the spiroid 28 and to be transferred along the length 27. Preferably, the gas phase 44 is also transferred. During rotation, the liquid phase 46 remains in the lowest part of the apparatus 20 due to gravity. Rotation effects mixing normal to the axis of rotation 30. The spiroid 28 causes the gas phase 44 and liquid phase 46 to be moved from the proximal end 23 to the distal end 25. As the spiroid 28 transfers the gas phase 46 and the liquid phase 44, the gas phase 44 and the liquid phase 46 in the reaction chamber 24 flow from the distal end 25 towards the proximal end 23 occurs. Thus, mixing is achieved both normal to the axis of rotation 30 and along the length 27.

Figure 2:
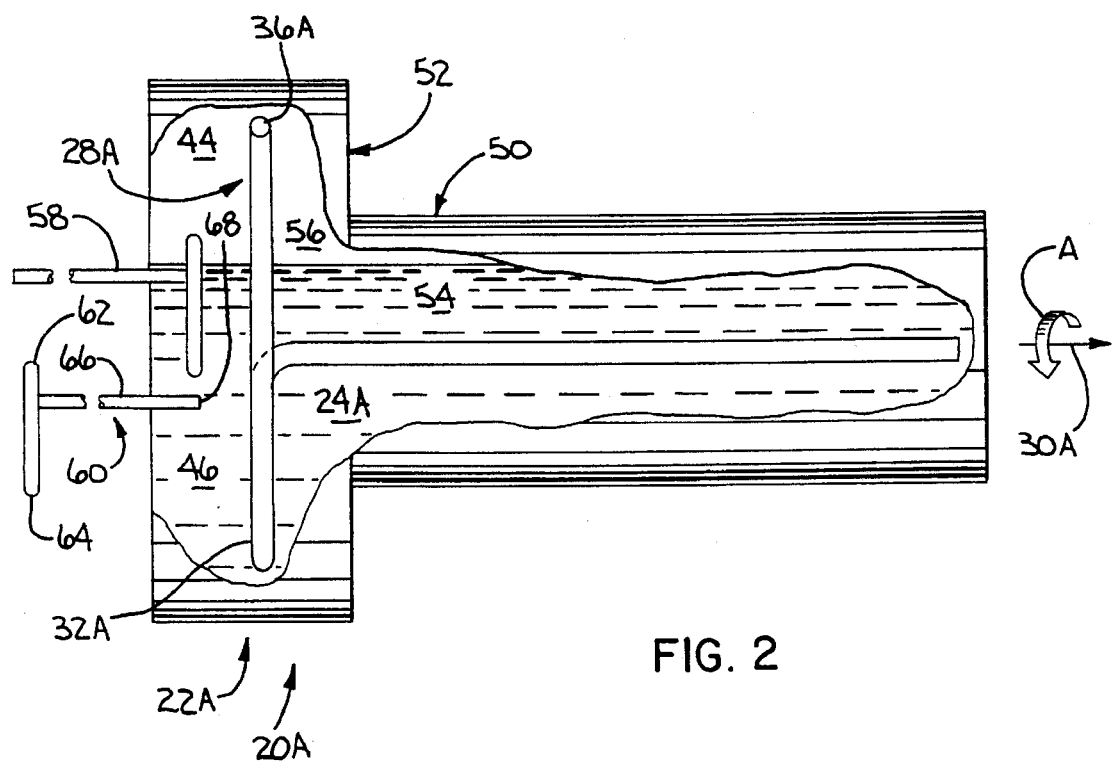
FIG. 2 is a partially broken away side view of an alternative embodiment of a reactor providing for gas and liquid introduction and removal, and for internal recirculation and mixing of reactants.

FIG. 2 illustrates a preferred embodiment of the reactor 20A. The reaction vessel 22A has first and second parts 50, 52 that define first and second compartments 54, 56, respectively, of the reaction chamber 24A that are in fluid and gaseous communication with each other. The first and second parts 50, 52 preferably have a round cross section in a plane normal to the axis of rotation 30A. The cross-sectional area of the first part 50 is less than the cross-sectional area of the second part 52 which acts as a rotating reservoir.

The recirculation spiroid 28A is shown entirely within the reaction chamber 24A. The inlet 36A is within the second compartment 56 and the coil 32A has a diameter greater than that of the first compartment 54. When the first compartment 54 is completely filled with liquid phase 46 the inlet 36A goes through the gas phase 44 in the second compartment 56. Further, if the constant liquid level in the first compartment 54 is held quite low the recirculation spiroid 28A still remains fully functional.

A discharge 58, illustrated as a spiroid, transfers gas phase 44 and liquid phase 46 from the reaction chamber 24A to the exterior of the reaction vessel 22A. The discharge 58 is preferably operably associated with the reaction vessel 22A so that rotation of the reaction vessel 22A causes the discharge 58 to transfer an aliquot of the gas phase 44 and the liquid phase 46 to the exterior of the reaction vessel 22A with each rotation.

The reactor 20A also includes a feed spiroid 60 having an inlet 62 exteriorly located from the reaction chamber 24A, at least one coil 64 attached to an elongate feed element 66 and an outlet 68 on the feed element 66 and distal from the coil 64. The feed spiroid 60 is operably associated with the reaction vessel 22A so that rotation of the reaction vessel 22A causes rotation of the feed spiroid 60. As discussed in more detail below, rotation of the feed spiroid 60 causes additional gas and liquid phases to be introduced into the reaction chamber 24A. The steady state medium and gas removal through 58 exactly equals the input through 66.

Figure 3:
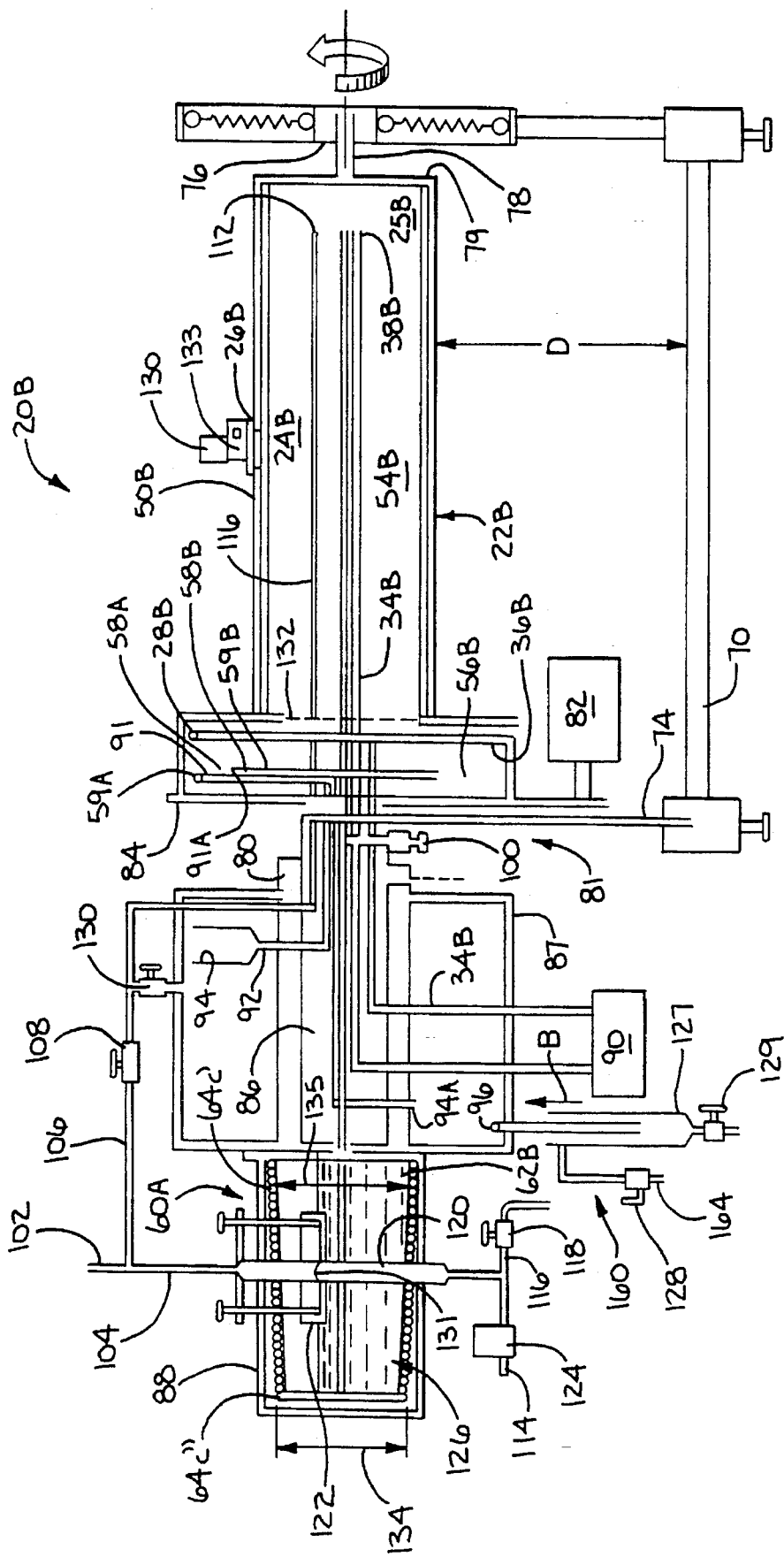
FIG. 3 is a side sectional view of a preferred embodiment of the reactor.

FIG. 3 illustrates a most preferred embodiment of the reactor 20B. The reaction vessel 22B is supported on a base 70 by an upright spring gimbal support 72 and an upright housing support 74. A spring mounted gimbal bearing 76 on the gimbal support 72 rotatably receives and supports a shaft 78 that extends from a distal end 79 of the reaction vessel 22B.

Extending from a proximal end 81 of the reaction vessel 22B is a rotatable shaft 86 passing through a stationary housing 80 that rests on the housing support 74. The rotatable shaft 86 which extends through the stationary housing 80 is attached to the reaction vessel 22B so that rotation of the reaction vessel 22B causes rotation of the shaft 86. As discussed below, the shaft 86 receives elements of the recirculation spiroid 28B, feed spiroid 60 and two discharges 58A and 58B.

A driven sprocket 84 is attached to the reaction vessel 22B and is operably associated with a variable speed motor 82 mounted on the housing support 74. The sprocket 84 rotates in response to the variable speed motor 82. Rotation of the sprocket 84 causes the reaction vessel 22B and the shaft 86 to rotate.

The reaction vessel 22B partially extends into and rotates within a stationary receptacle 87, and a stationary feed reservoir 88. Where liquid or gas transfer between a rotating and stationary tube are required this is accomplished by terminating the tube in an annular slot cut into the rotating shaft which mates with a tube in the stationary journal in which the shaft turns (See, FIG. 4A to 4E).

The recirculation spiroid 28B has an inlet 36B located within the second compartment 56B of the reaction vessel 22B. The elongate recirculation element 34B extends through the shaft 86, through a stationary sampling block 90, back through the shaft 86, into the reaction chamber 24B and terminates at the distal end 25B of the reaction chamber 24B through the outlet 38B. Thus, a segment of the recirculation spiroid 28B is stationary and located exteriorly of the reaction chamber 24B providing external access through the stationary sampling block 90 to the constantly circulating gas and liquid contents of the reaction vessel 22B.

The reactor 20B has two discharges 58A and 58B, of which only one is used at a time and the other is plugged. The selection as to which of the discharges 58A or 58B is used is dependent on the level of the liquid phase that is desired in the reaction chamber 24B. The discharge 58A has a discharge inlet 91 within the second compartment 56B. The discharge of 58A terminates in an outlet 94 that is at the end of an internal standpipe 92. The internal standpipe 92 is employed to accommodate greater liquid levels in the reaction chamber 24B. The internal standpipe 92 creates a liquid head therein which must be overcome so that gas and liquid phases will be transferred from the reaction chamber 24B through the discharge 58B, overflow the standpipe 92 and enter the stationary receptacle 87. Preferably, the internal standpipe 92 is slightly flared open at the outlet 94 so that gas phase can exit the standpipe 92 without causing material loss of the liquid head in the standpipe 92, and attendant gas pressure loss in the reactor chamber 26B. In this configuration uptake loop 151 (See, FIG. 4E) is used.

A drain 96 in the receptacle 87 is in fluid and gaseous communication with the standpipe 92. The gas and liquid phases coming through the drain 96 flow into an auxiliary adjustable external standpipe 127 which is capable of movement as indicated by the arrow B. The standpipe 127 also has an extension 160 that terminates in a valve 128 and drain 164 to provide further adjustment of the liquid level in the stationary receptacle 87.

Figure 4D:
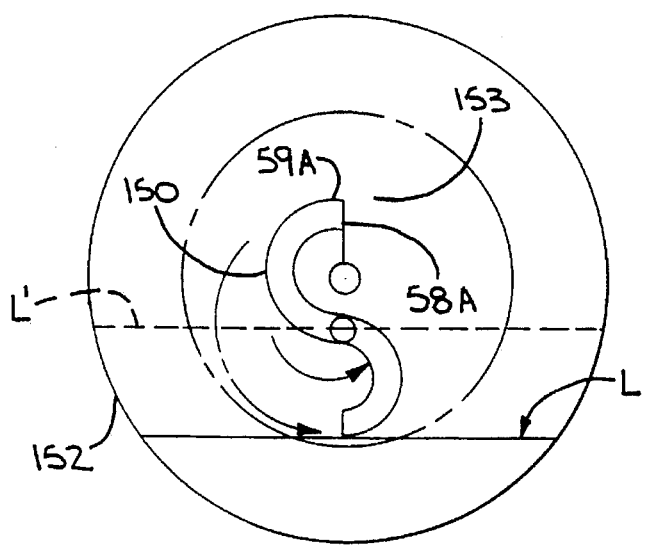
FIGS. 4A to 4E are diagrammatic representations of different discharge uptake coils and discharge configuration which control liquid levels and a cross section of a seal.
Figure 4E:
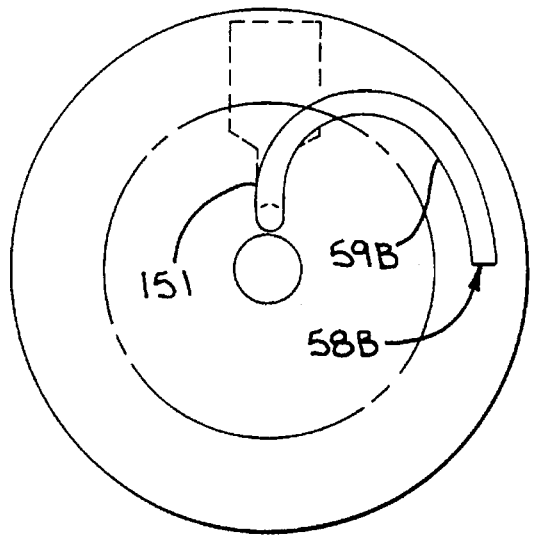
Figure 4A:
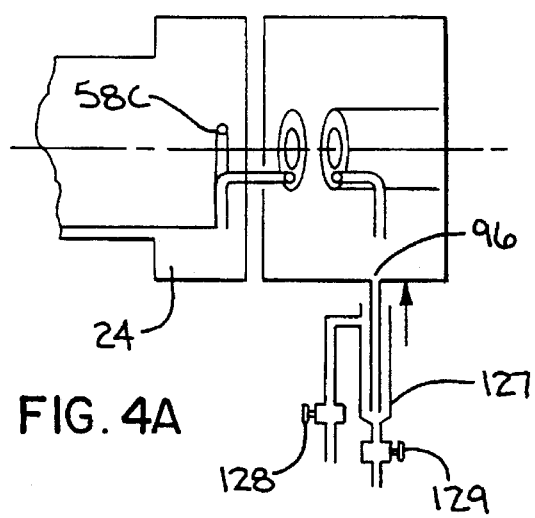
Figure 4C:
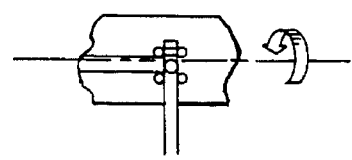
Figure 4B:
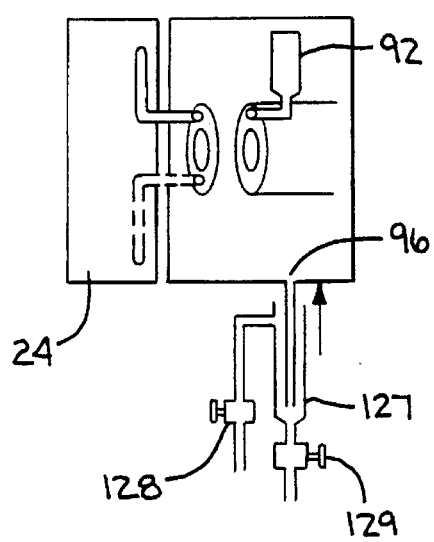

A second adjustable source of discharge back pressure may be provided by an adjustable external standpipe 127, this external standpipe provides for adjustment of the gaseous pressure and attendant liquid medium level within the bioreactor during operation beyond levels attainable from the fixed standpipe 92 (See, FIG. 4B and 4E also). Appropriate dimensioning of these two standpipes insures that the hydrostatic gas back pressures obtainable from these two standpipe sources can not exceed the delivery pressure of the fresh medium input spiroid.

When it is desired to operate the reactor chamber less than half full of liquid medium and at ambient pressure the discharge 58B can be used. The inlet 91A is located within the second compartment 56B and is in fluid and gaseous communication with the outlet 94A. Gas and liquid phases passing through the discharge 58B exit at the outlet 94A flowing into the receptacle 87 and then the drain 96 with valve.

To so operate the bioreactor at ambient pressure the plug (not shown) is removed from discharge 58B (FIG. 3) and placed in discharge 58A after removal of uptake loop 151 (FIG. 4E). The offset discharge dipping loop 150 (FIG. 4D) is inserted into the discharge port 58B (FIG. 3). Referring to FIG. 4D, the first intake 152 of this dipping loop 150 may be utilized so that its maximum depth of immersion in the liquid medium is maintained as illustrated with the liquid medium being at level L. Alternatively, the second inlet 153 can be utilized so that the minimum depth of immersion is maintained with the liquid medium level being at level L' (shown in phantom). The first and second inlets 152, 153 can be used to achieve a level between the maximum and minimum. When such a configuration is used with ambient gas pressures in all chambers, both rotating and stationary, then no liquid pistons form in the dipping loop 150 rather there is continuous gas communication between all chambers at all times.

Referring back to FIG. 3, a gas line 102 provides an alternative source of the fresh gas phase to the feed reservoir 88 through a gas feed reservoir leg 104 and to the reaction chamber 22B through a reaction chamber leg 106. The reaction chamber leg 106 is in fluid communication with an elongate gas tube 110 that terminates at an outlet 112 at the distal end 25B of the reaction chamber 24B. A shutoff valve 108 can be used to control the flow of gas phase through the reaction chamber leg 106.

When the alternative gas supply is employed and the liquid medium level in the reaction chamber 24 is above the auxiliary gas supply outlet 112, discharge is through the interior standpipe 92. The stationary chamber air inlet valve 130 should be opened. Gas and liquid phases pass through the auxiliary standpipe 127 with valve 129 closed and the liquid/gas exhaust side arm valve 128 should be opened. When such auxiliary gassing is taking place a sufficient auxiliary liquid head ($H_A$) should be maintained in the auxiliary external standpipe 127 to offset the increased gas pressure in the reaction chamber derived from use of the auxiliary gas supply.

The feed reservoir 88 is connected to the receptacle 87 and stationary housing 80. A liquid feed line 114 supplies the feed reservoir vessel 88 with fresh liquid phase. The liquid phase in the feed reservoir vessel 88 can be drained using liquid drain line 116 that has a shut off valve 118. A sight glass 120 is used to view the liquid and gas levels in the feed reservoir 88. The level of liquid phase in the sight glass 120 is the same as that in the feed reservoir 88. An adjustable feed reservoir level control 122 (shown schematically) for controlling the liquid level in the reservoir vessel 88 is located on the sight glass 120. A preferred level control 122 is a focused photoelectric eye (not shown) that senses the meniscus 131 of the liquid phase in the sight glass 120. The level control 122 is manually raised or lowered to obtain the desired liquid level. As the meniscus 131 passes the focused photoelectric eye, a solenoid valve 124 located on the liquid feed line 114 is closed and opened to maintain the meniscus 131 at a fixed level and attain the desired liquid level in the feed reservoir 88. By controlling the level of liquid phase in the reservoir 88, the rate at which liquid and gas phases are transferred from the feed reservoir 88 to the reaction chamber 24B can be adjusted while maintaining the same speed of rotation.

A dimensioned spool 126 having the feed spiroid 60A wound upon it is rotatably received within the feed reservoir 88. The spool 126 is operably associated with the shaft 86 so that rotation of the shaft 86 causes the spool 126 to rotate and the feed spiroid 60A wound thereon to transfer liquid phase, and preferably also gas phase, from the feed reservoir 88 into the reaction chamber 24B. The feed spiroid 60A is discussed below. A feed shut off valve 100 can be turned on and off to permit or prohibit flow from the feed spiroid 60A into the reaction chamber 24B.

Preferably, the first part 50B of the reaction vessel 22B is transparent and permits observation of the contents within the first compartment 54B. The first part 50B is spaced from the top of the base 70 a distance D that permits the insertion of a microscope (not shown) capable of viewing the contents of the reaction chamber 24B. With some suspended cultures a coarse screen 132 spans the opening between the first compartment 54B and the second compartment 56B.

The general difference between pick up loops employed and resulting hydrostatic and pneumatic balance between a reactor running at ambient pressures with low and high reactor chamber liquid levels is shown in FIGS. 4A, 4D, 4B and 4E. FIGS. 4A and 4D show the low liquid level configuration. In this configuration there is no auxiliary liquid head in the auxiliary standpipe 127 or in the internal standpipe (not shown). Side arm valve 128 is closed and valve 129 is opened to permit direct drain through. The small radius pick up loop 59A of discharge 58C is employed. No liquid piston is formed in the pick up loop 59 and there is direct liquid and gaseous communication between the reaction chamber 24 and the drain 96. Liquid level in the reaction chamber 24 may be set between the liquid levels shown by placement of the small radius pick up loop 59A. If it is desired to operate the bioreactor at elevated pressures but in the low reactor liquid level configuration (with reference to FIG. 3) the gas pressure into gas inlet tube 102 and liquid inlet 114 are increased and valve 108 is opened as is stationary chamber gas inlet valve 130. The gas exhaust pressure is adjusted by the liquid level in the auxiliary standpipe 127. It is clearly apparent that with appropriate strength of construction of the reactor and gas pressure regulation of the collection vessel (not shown) into which drain 96 (FIG. 4A) empties that this reactor is readily adaptable to high pressure operation.

Referring to FIGS. 4B and 4E, with deep reactor medium levels the large radius pick up loop 59B is used. The small radius pick up loop which bypasses the interior standpipe is removed from the opening into which it was inserted. This opening is then plugged. The large radius pick up loop 59B is inserted into a rotating transfer opening in the rotating shaft which connects to the interior standpipe 92. Rotation of this large radius pick up loop 59B with respect to the shaft to control reactor liquid level is not shown. Such rotation is effective in controlling liquid level in the reaction chamber 24 but really only marginally so. The hydrostatics of this system are against maintenance of a high liquid level in the reaction chamber 24 unless this is accomplished by increasing the hydrostatic pressure the liquid in the reaction chamber 24 must overcome to be discharged. This is accomplished by addition of pneumatic pressure to the outlet of the internal standpipe 92. In effect the adjustable depth standpipe 127 does this.

The gas taken up by the discharge pick up loop 59B of discharge 58B is discharged through the internal standpipe 92 with each rotation. At equilibrium, liquid can be discharged through the internal standpipe 92 only when it overcomes the hydrostatic pressure from both the internal standpipe and the external adjustable standpipe 127. When valves 130 and 129 (FIG. 3) are closed the steady state high medium level must be such that the reactor chamber pneumatic pressure above the liquid therein does not exceed the maximum delivery pressure of the feed spiroid (not shown).

Figure 10A:
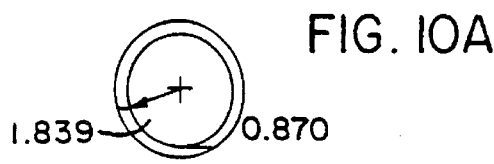
FIGS. 10A to 10V are depictions of the nature and amount of liquid and gas, in each coil, the displacement of the liquid piston in each coil and the hydrostatic head deriving from the displacement for a particular spiroid having 22 coils.
Figure 10B:
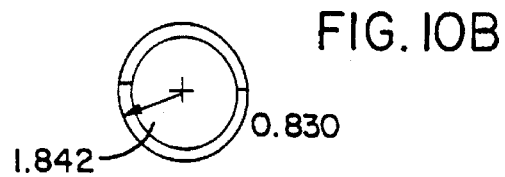
FIG. 10W is a legend for FIGS. 10A to 10V.
Figure 10C:
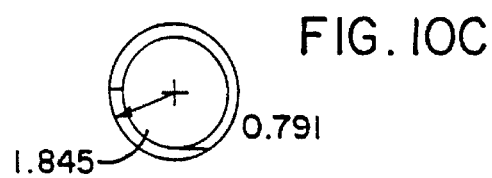
Figure 10D:
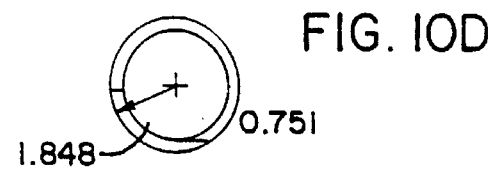
Figure 10E:
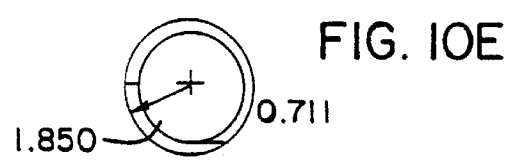
Figure 10F:
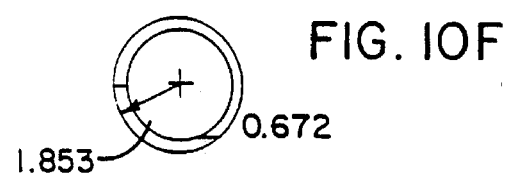
Figure 10G:
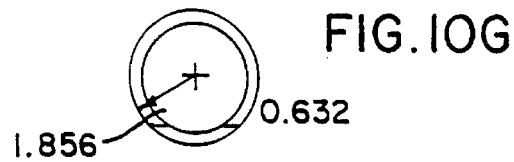
Figure 10H:
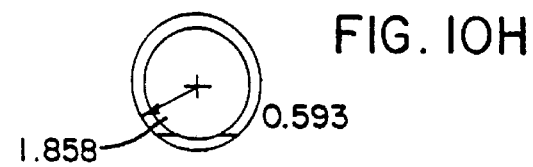
Figure 10I:
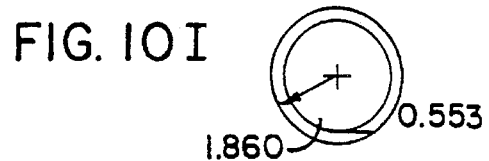
Figure 10J:
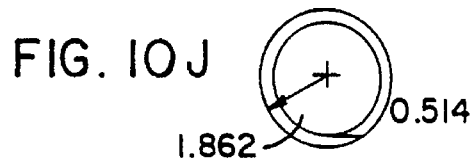
Figure 10K:
Figure 10L:
Figure 10M:
Figure 10N:
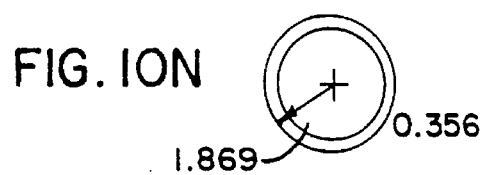

Referring to FIG. 3, the feed spiroid 60A has coils 64C that are wound around the spool 126. The spool 126 is appropriately tapered so that the diameter 135, and hence the diameter of the coil 64C', adjacent the intake 62B is greater than the diameter 134 adjacent to discharge coil 64C". This decrease in volume of each successive coil due to each successive reduction in diameter increases the percentage of each successive coil that is filled by the liquid piston (not shown) as it moves from the coil 64C' adjacent to the larger diameter 135 to coil 64C" which is adjacent the smaller diameter 134. This precise volume decrease in each coil, as illustrated in FIG. 10A to 10V, from uptake through discharge balances the absolute gas pressure in the coils with the hydrostatic pressure therein when a defined low liquid uptake volume is employed.

Rotatable seals are provided to permit fluid and gaseous communication with the interior of the shaft 86 as required. FIG. 4C shows a typical cross section of such a seal.

The parts of the reactor 20B that come in contact with the gas and liquid phases can be sterilized by removing the photoelectric level control 122, the coil of the solenoid valve 124, and then removing the remainder of the bioreactor from the base 70, gimbal and housing supports 72 and 74 and autoclaving the remainder. After autoclaving the remainder is easily replaced in the base for reuse. Where size of the reactor precludes removal it may be steam sterilized in place.

Referring to FIG. 3, in operation after sterilization, the reactor 20B is set to operate at the desired steady state reactor liquid medium level. With the gas of choice connected to gas line 102 and the liquid medium supply connected to liquid feed line 114, the machine is run at the desired fresh medium feed rate until the appropriate steady state liquid level in the reaction chamber 24B is reached. At that time rotation is stopped with the chamber cap 26B pointing up, the chamber port valve 130 is opened and inoculum is aseptically introduced through the capped chamber septum 133. This is usually done against a slight positive pneumatic pressure of sterile gas to insure asepsis during inoculation after which the chamber port valve is closed and the chamber septum recapped. The medium feed shutoff valve 100 is generally closed during initial culture growth but a low flow rate of gas through the elongate tube 110 is continued. The operation of the recirculation spiroid is unaffected by fresh medium.

When the population of the organism is such, as indexed by direct counts or medium composition as determined from medium passing through the sampling chamber 90, the fresh medium feed shutoff valve 100 is fully opened and perfusion commences at the prescribed rate based on the rate of rotation and the liquid and gas levels in the feed reservoir 88.

When so operating all bioreactor systems work in unison. Fresh medium input rate, governed by the rate of rotation of the feed spiroid 60A and the depth of the medium in the fresh medium feed reservoir 88 which is closely controlled by the opening and closing of solenoid valve 124 which in turn is controlled by the photoelectric level control 122 which is actuated by the meniscus 131 in the sight glass 120. Liquid and gas taken up during each rotation of the fresh medium feed spiroid 60A is propelled to the distal end 25B of the reaction chamber 24B where it is discharged. Pressure characteristics of this discharge of fresh medium into the reaction chamber 24B are dependant upon the geometry of the feed spiroid 60A.

The liquid level in the reaction chamber 24B is maintained by the shape of the pick up loop 59A,59B of the discharge 58A,58B and the magnitude of the adjustable back pressure against which the chosen discharge 58A,58B operates. The system is designed so that this back pressure acting against the discharge 58A,58B cannot exceed that provided by the feed spiroid 60A. The liquid level in the reaction chamber 24B and the pneumatic pressure of the gas above this liquid medium are in steady state conditions. Under some conditions of operation, for example where the reaction chamber 24B steady state liquid level is well above the axis of rotation of the reaction chamber 24B and the auxiliary gas supply through outlet 112 is used, the steady state liquid level might be altered. In such cases the steady state level desired may be reestablished by balancing the gas pressure increase in the reaction chamber 24B with a corresponding increase in the housing 80 through adjustment of the auxiliary adjustable standpipe 127.

Back pressure does not affect per rotation delivery rates of gas and liquid by the fresh medium uptake spiroid as long as the back pressure does not exceed the delivery pressure of the uptake spiroid.

With a constant rate of rotation and the liquid level in the reaction chamber at a steady state, the rate of flow and relative balance of gas and liquid passing through the sampling chamber 90 is constant as is the rate of recirculation from proximal to distal end 25B of the reaction chamber 24B. This recirculation rate within the reaction chamber 24B is unaffected by rate of liquid medium and gas input into and removal from the reaction chamber.

FIG. 5A to C illustrate that the spiroid can have various shapes. Spiroid 136A (FIG. 5A) is a helix whose coils 138A can be imagined to have been wound about a cylinder. The spiroid 136B (FIG. 5B) can be imagined to have had its coils 138B wound around a truncated cone. The spiroid 138C (FIG. 5C) is a spiral whose coils 136C are all in a single plane. The spiroids used herein can have any of these shapes or their intermediates.

FIGS. 6A and B show an attachment insert spiroid 134 inserted into the cylindrical reaction chamber 22B to provide greater surface area for the growth of attachment dependent cells. The insert spiroid 134 is dimensioned so that the rectangular cross section taken parallel to the axis of rotation 30B (which extends out of the page) of its opening steadily decreases from the uptake opening 136 to the discharge opening 137. This decrease in cross-sectional area is designed so that the angular velocity of the liquid and gas phases flowing from the uptake opening 137 to the discharge opening 138 is constant. This is done so that cells attached to the insert spiroid surfaces 140 and the interior surface 142 of the reaction vessel 22B have a constant rate of flow of liquid and gas over them regardless of where the cells are attached. This configuration is required to compensate for the obvious condition that the further one proceeds toward the axis of rotation 30B of the reaction vessel 32B, the less distance the liquid and gas phases travel during a given rotation. In any coil of the insert spiroid 134, the velocity of liquid flow over insert spiroid surfaces 140 may be proportionately increased by appropriately decreasing the rectangular cross section. This derives from the fact that when operating, the exact volume of liquid and gas phase taken up by the uptake opening 136 during a revolution is discharged from the insert spiroid 134 during a subsequent revolution.

In operation the depicted attachment insert spiroid 134 rotates with the reaction vessel 22B within which it is inserted. With the insert spiroid 134 in place, the reaction vessel 22 is attached to the reactor 20B (FIG. 3). Supports 144 (FIG. 6B) of the insert spiroid 134 are tightly sealed and fit snugly against the reaction vessel interior surface 142. The fresh medium introduction tube, the auxiliary air supply tube and the recirculation return tube all pass through the central cavity of the insert 146. The insert spiroid 134 is somewhat shorter than the reaction vessel 22B so that liquid and gas phases discharged into the central cavity 146 of the insert spiroid 134 can drain out the ends of the insert spiroid 134. The supports 144 are provided with one or more cut outs 145 so that lateral movement and mixing of liquid and gas is not impaired.

With cultures where cells are grown in suspended culture the change in rate of nutrient flow over the side walls of the inserted spiroid is of no material consequence since the suspended cells are free floating in the medium.

This sort of reaction chamber insert (FIG. 16A and 16D) is used primarily to increase the gas liquid interface and gas dissolution in the medium permitting the support of the higher density populations of the culture. Such inserts (FIGS. 16A and 16D) may be made from round uniform bore tubing wound into planar spirals (FIG. 16A). When such spirals are inserted so they abut against one another (FIG. 16C) they form a second non-circular (FIG. 16B) cavity and completely fill the reactor chamber except for space allowed for fluid and gas return on each end (FIG. 16C).

Liquid Head (Hydrostatic Pressure)

The liquid volume in each coil of a spiroid is constant during steady state operating conditions and forms a liquid phase piston (plug) in the coil that prohibits gas phase from bubbling backwards in the opposite direction the liquid phase is traveling. The gas volume taken up by the inlet into the coil during each rotation is of a constant volume but must be reduced in volume in each successive coil if a liquid head (hydrostatic pressure) is to be developed in each coil. The development of liquid head requires a gas pressure differential between the gas phase in front of and behind the constant volume liquid piston in each coil. This gas pressure differential equals the liquid head. The liquid heads in the coils are additive as are the gas pressure differentials. The design of a balanced spiroid requires the balancing of hydrostatic pressures and gas pressures in each successive coil of the spiroid. The following example, provided by way of illustration and not limitation, explains the designing of the feed spiroid, including the required balancing. It is understood that the example applies to spiroids in general and the feed spiroid in particular.

EXAMPLE 1: DESIGN OF THE FEED SPIROID

Values for variable parameter, e.g., the minimum hydrostatic pressure, the internal diameter (I.D.) of the feed reservoir, the liquid delivery rate, the I.D. and the outer diameter (O.D.) of the tubing from which the spiroid is made and the like, have been selected for the design of a particular feed spiroid to make the discussion and equations easier to understand. Obviously, the selection of the parameter values can be changed to suit the requirements of the spiroid.

Preferably, the feed spiroid is capable of delivering liquid phase to the reaction vessel over a wide range of per rotation delivery rates with a minimum hydrostatic pressure of about 10 inches (28.4 cm) of water. Further, the spiroid must turn within a 4" (10.2 cm) diameter cylindrical feed reservoir vessel and preferably delivers about 300 milliliters (ml.) of liquid per 1440 revolutions per day.

Tubing Size

Using a 2" turning radius of the inlet in the liquid in the feed reservoir, a first approximation of the volume of closure of a circular segment, i.e., a liquid phase plug, of the circumference of a coil of ¼" O.D.×⅛" I.D. tubing is found to be about 0.2 ml. This yields a 1 rpm delivery of about 290 ml per day.

Using ¼" O.D.×⅛" I.D. tubing and the 4" limit on the feed spiroid's outside diameter, the radius of the centerline of the tubing is 1.875". The value of $\alpha$, the half angle of closure may be determined from the equation:

$$\alpha = \cos^{-1}\left(\frac{R_n - r}{R_n}\right)$$

Where: $\alpha$ is one half the minimum angle of closure; $R_n$, is the radius of the centerline of the tubing forming the inlet coil and, r is the inside radius of the tubing. See, FIG. 7A.

Determining the Required Number of Coils and the Attainable Liquid Head Increment The minimum total liquid head (hydrostatic pressure) required is stipulated as 10". The maximum liquid head that can be developed in an individual coil is the diameter of the centerline of the discharge coil (the last coil of the spiroid) less the inside diameter of the discharge coil. The total liquid head is the sum of the uniform individual liquid heads developed in each coil. For a spiroid having N coils, that is:

$$Ht = \Sigma n_i \Delta h_i$$

Where: Ht is the total liquid head; $n_i$ is an individual coil; and $\Delta h_i$ is the incremental liquid head of the individual coil. If $\Delta h$ is held uniform between successive coils containing a constant liquid volume then:

$$\Sigma n_i = N\left(\frac{1+N}{2}\right) \text{ and } \Delta h_i = \frac{Ht}{N\left(\frac{N+1}{2}\right)}$$

If there is to be "space" in the discharge coil for increased liquid delivery from increased immersion of inlet coil then:

$$2(R_1 - r) \geq Q(N\Delta h)$$

Where: $R_1$ is the radius of the centerline of the tube forming the discharge coil; r, the inside radius of the uniform bore tubing; Q is a multiplier determined by the following:

$$Q = 1/DI$$

where DI is the portion off the maximum possible liquid head in the discharge coil to be attained when the spiroid is in a low liquid delivery rate configuration; N is the number of coils in the spiroid; and $\Delta h$ the increment of head in each coil. (The argument above develops from the fact that the maximum liquid head the discharge coil will support is twice the centerline radius of that coil less the inside diameter of the tubing of which the spiroid is to be made.)

Wherein for a spiroid having coils made of tubing, one of the coils being an inlet coil and another coil being a discharge coil, with the inlet of the inlet coil being positioned in the reservoir vessel and the outlet on the discharge coil being positioned in the reaction chamber, the minimum number of coils (N) for the spiroid having a stipulated total liquid head ($H_t$), assuming that the change in head ($\Delta h$) between each successive coil is held uniform, is determined by $$2(R_1 - r) = Q(2H_t/N + 1),$$

where $R_1$ is the radius of the centerline of the tubing of the discharge coil; r is the inner radius of the tubing; $H_t$ is the stipulated total liquid head the spiroid is to deliver; N the minimum number of coils of the spiroid; Q is the reciprocal of the fraction of the maximum head ($2(R_1-r)$) the discharge coil can reach when the spiroid is balanced with respect to hydrostatic and pneumatic pressures.

In this example let Q=4. It is known a priori that $R_1 < R_n$. Since $R_n = 1.875"$, $r = 0.0625"$ and $H_t = 10"$ $$2(R_1 - r) = \frac{80}{N+1} \; ; R_1 - r = \frac{40}{N+1}$$

$R_1 - r < R_n - r$ so:
$1.8125 > R_1 - r$
$1.8125 > \frac{40}{N+1}$ ; $1.8125 N > 38.1875; N > 21.07$ Using the next whole number value, an N of 22 is acceptable. An average liquid head increment of 0.039526" (10"/253) is required. The determination denominator (253) is discussed below in the section entitled "Balancing".

With this $\Delta h_i$ the required liquid arc (and hence the radius $R_1$) through which the discharge coil turns can be calculated based upon the liquid head alone. But, considering liquid heads as independent from gas pressures can constitute an egregious error. For hydrostatic and gas pressures must be in agreement (in balance) within and between the various coils of the spiroid to pump liquid and gas against a liquid head.

Balancing

In any coil of the spiroid under consideration, the total length of the centerline of any coil may be designated as $S_T$ (FIG. 8 and TABLE 2, below). The length of the centerline of the liquid and gas in the coil can be designated as $S_G$ and $S_L$, respectively. Since the tubing has a uniform bore, the volume of the gas may be stated in Boyle's law in terms of $S_G$ and Boyle's law applied to the inlet and discharge coils of the example spiroid is:

$$P_1/P_{22} = S_{G22}/S_{G1}$$

The discharge coil numbered 1 has a liquid head of 22$\Delta$h and the inlet coil numbered 22 has a liquid head of 1$\Delta$h. Since these head increments are additive, coil 1 has 253$\Delta$h gas pressure above the liquid pistons; coil 2, 231$\Delta$h and so on up to coil 21 with 3$\Delta$h and coil 1 with 1$\Delta$h. The liquid head within coils 1, 2, 21, and 22 is 22$\Delta$h, 21$\Delta$h, 2$\Delta$h, and 1$\Delta$h, respectively (See, TABLE 1, below). In calculating gas pressures, the $\Sigma\Delta$h in the coil is used.

For example: The absolute pressure in coil 22 is:

$$P_{22} = \frac{(23-22)\Delta h}{406.782480} + 1 \text{ since:}$$

1 atm = 406.782480 inches of H$_2$O

TABLE 1

Recursively calculated values for a 22 coil "balanced" spiroid delivering liquid against a minimum hydrostatic pressure of 10 inches of water with a uniform head increment of a head ($\Delta$h)* in each coil.

| NUMBER OF COILS | CUMULATIVE NUMBER OF HEAD INCREMENTS | INCHES TURNING RADIUS | ATMOSPHERIC PRESSURE IN COIL |
| --- | --- | --- | --- |
| 1 | 253 | 1.8394 | 1.024583 |
| 2 | 231 | 1.8424 | 1.022445 |
| 3 | 210 | 1.8453 | 1.020405 |

TABLE 1-continued

Recursively calculated values for a 22 coil "balanced" spiroid delivering liquid against a minimum hydrostatic pressure of 10 inches of water with a uniform head increment of a head ($\Delta h$)* in each coil.

| NUMBER OF COILS | CUMULATIVE NUMBER OF HEAD INCREMENTS | INCHES TURNING RADIUS | ATMOSPHERIC PRESSURE IN COIL |
|---|---|---|---|
| 4  | 190 | 1.8481 | 1.018462 |
| 5  | 171 | 1.8508 | 1.016615 |
| 6  | 153 | 1.8533 | 1.014866 |
| 7  | 136 | 1.8557 | 1.013215 |
| 8  | 120 | 1.8580 | 1.011660 |
| 9  | 105 | 1.8601 | 1.010202 |
| 10 | 91  | 1.8621 | 1.008842 |
| 11 | 78  | 1.8639 | 1.007579 |
| 12 | 66  | 1.8656 | 1.006413 |
| 13 | 55  | 1.8672 | 1.005344 |
| 14 | 45  | 1.8687 | 1.004372 |
| 15 | 36  | 1.8699 | 1.003498 |
| 16 | 28  | 1.8711 | 1.002721 |
| 17 | 21  | 1.8721 | 1.002040 |
| 18 | 15  | 1.8730 | 1.001457 |
| 19 | 10  | 1.8737 | 1.000972 |
| 20 | 6   | 1.8743 | 1.000583 |
| 21 | 3   | 1.8747 | 1.000291 |
| 22 | 1   | 1.8750 | 1.000097 |

*$\Delta h = 0.039525692''$ $$\alpha_1 = \text{Cos}^{-1}\left(\frac{R_1 - r}{R_1}\right)$$

and $$\beta_1 = \text{Cos}^{-1}\left(\frac{R_1 - r - 22\Delta h}{R_1}\right)$$

The appropriate first estimate balancing value for $R_1$ can be determined by starting with $R_{22}$ (a known value) as an estimate of $R_1$. $S_L$ can be determined from $$S_L = \left(\frac{\alpha + \beta}{360}\right) S_{T22}$$

Using this $S_L$ value, a value for $S_{G22}$ can be determined:

$$S_{T22} = 2\pi R_{22}$$

and $$S_{G22} = S_{T22} - S_{L22}$$

Using this $S_{G22}$ value and the Boyle's law relationship, $S_{G1}$ is estimated by EQUATIONS 1 and 2:

$$S_{G1} = \left(\frac{P_{22}}{P_1}\right) S_{G22} \qquad \text{(Equ. 1)}$$

TABLE 2

Dimensions of a continuous spiroid which is balanced with respect to hydrostatic and gas pressures when so immersed during rotation that the arc length through the liquid phases equal 2.810290*

| COIL NUMBER | $\theta, 2\pi$ INCREMENTS START | FINISH | RADIUS START | FINISH | CORRECTED $\theta$ VALUES START | FINISH | NUMBER OF TURNS | LENGTHS SPIRAL | ACTUAL |
|---|---|---|---|---|---|---|---|---|---|
| 1  | 0.000000   | 6.283185   | 1.839384 | 1.842417  | 0.000000   | 6.299877   | 1.002657  | 11.597539 | 11.600249 |
| 2  | 6.283185   | 12.566371  | 1.842417 | 1.845325  | 6.299877   | 12.599754  | 2.005313  | 11.616303 | 11.619007 |
| 3  | 12.566371  | 18.849556  | 1.845325 | 1.848106  | 12.599754  | 18.899531  | 3.007970  | 11.634264 | 11.636964 |
| 4  | 18.849556  | 25.132741  | 1.848106 | 1.850757  | 18.899631  | 25.199580  | 4.010626  | 11.651649 | 11.654245 |
| 5  | 25.132741  | 31.415927  | 1.850757 | 1.853279  | 25.199580  | 31.449385  | 5.013283  | 11.667613 | 11.670305 |
| 6  | 31.415927  | 37.699112  | 1.853279 | 1.855669  | 31.449385  | 37.799262  | 6.015939  | 11.683248 | 11.685936 |
| 7  | 37.699112  | 43.982297  | 1.855669 | 1.857926  | 37.799262  | 44.099139  | 7.018596  | 11.697912 | 11.700597 |
| 8  | 43.982297  | 50.265482  | 1.857926 | 1.860049  | 44.099139  | 50.399017  | 8.021253  | 11.711731 | 11.714413 |
| 9  | 50.265482  | 56.548668  | 1.860049 | 1.862036  | 50.399017  | 56.698849  | 9.023909  | 11.724608 | 11.72787  |
| 10 | 56.648668  | 62.831853  | 1.862036 | 1.863887  | 56.698849  | 62.998771  | 10.026566 | 11.736876 | 11.739552 |
| 11 | 62.831853  | 69.115038  | 1.863887 | 1.865600  | 62.998771  | 69.298646  | 11.292222 | 11.748022 | 11.750696 |
| 12 | 69.115038  | 75.399224  | 1.865600 | 1.867174  | 69.298646  | 75.598525  | 12.031879 | 11.758387 | 11.761058 |
| 13 | 75.399224  | 81.681409  | 1.867174 | 1.868609  | 75.598525  | 81.898402  | 13.034535 | 11.767861 | 11.770530 |
| 14 | 81.681409  | 87.964594  | 1.868609 | 1.869904  | 81.898402  | 88.198279  | 14.037192 | 11.776453 | 11.779120 |
| 15 | 87.964594  | 94.247780  | 1.869904 | 1.871058  | 88.198279  | 94.498156  | 15.039849 | 11.784154 | 11.786820 |
| 16 | 94.247780  | 100.570965 | 1.871058 | 1.872070  | 94.498156  | 100.798033 | 16.042505 | 11.790955 | 11.801620 |
| 17 | 100.570965 | 106.814150 | 1.872070 | 1.872940  | 100.798033 | 107.097910 | 17.045162 | 11.796865 | 11.799528 |
| 18 | 106.814150 | 113.097336 | 1.872940 | 1.873667  | 107.097910 | 113.397787 | 18.047818 | 11.801868 | 11.804530 |
| 19 | 113.097336 | 119.380521 | 1.873667 | 1.874251  | 113.397787 | 119.697664 | 19.050475 | 11.805966 | 11.808627 |
| 20 | 119.380521 | 125.663706 | 1.874251 | 1.8745691 | 119.697664 | 125.997542 | 20.053131 | 11.809156 | 11.811816 |
| 21 | 125.663706 | 131.946892 | 1.874691 | 1.874988  | 125.997542 | 132.297419 | 21.055788 | 11.811433 | 11.814095 |
| 22 | 131.946892 | 138.230077 | 1.874988 | 1.875000  | 132.297419 | 138.597296 | 22.058442 | 11.812800 | 11.815459 |
|    |            |            |          |           |            |            |           |           | 258.252454 |

In calculating liquid head in a coil, the equation $(23-n)\Delta h$ is used. Effecting correspondence between liquid head in a given coil and the coil number with the equation $(23-n)\Delta h$ the $\alpha$ and $\beta$ values for coil 1 may be calculated from the equations:

and $$R_1' = \frac{S_{G1} + S_L}{2\pi} \qquad \text{(Equ. 2)}$$

Using this $R_1$ value, $\alpha_1$ and $\beta_1$ are reestimated as is $S_L$ by:

$$S_L' = \left( \frac{\alpha_1' + \beta_1'}{360} \right) 2\pi R_1'$$

Using this, $S_L'$ value, $S_{G22}$ is reestimated and $R_1''$ is determined as in EQUATIONS 1 and 2, above.

Through recursive estimation, the value of $R_1$ and $S_L$ can be determined as constant to any degree of accuracy desired.

When a constant $S_{LC}$ is determined, a constant value for $S_{G22}$ is likewise determined and liquid head is balanced with the gas pressure required in the inlet and discharge coils.

Acceptable radii for the intervening coils can be calculated from:

$$S_{Gn} = \left( \frac{P_{22}}{P_n} \right) S_{G22}$$

$$R_n = \frac{S_{Gn} + S_{LC}}{2\pi}$$

A coil by coil diagram of such a balanced spiroid (FIGS. 9 and 10A to 10V) and the tabular values associated with FIG. 10A to 10V (TABLE 2) convert the spiroid to a continuum and address the lateral (z-axis) offset and the differences in $\beta$ in successive coils.

The spiroid tested (FIGS. 11 to 14) was predicated upon this expanded and refined approach.

Figure 9:
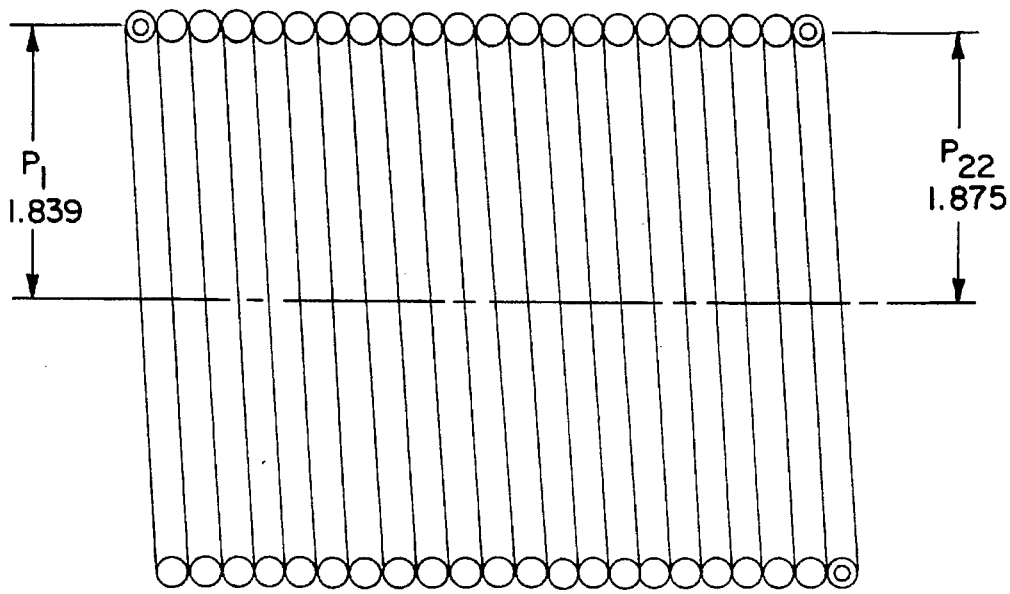
FIG. 9 is a depiction of a spiroid which would display balance between absolute gas pressure and liquid head when submerged to 1.119 cm.

The spiroid of FIG. 9 and TABLE 2 when submerged to a depth which will provide a tubing central axis length of 2.810290 inches through the liquid piston will produce a liquid piston that will effect virtually perfect balance with respect to gas and hydrostatic pressures as diagramed (FIGS. 9 and 10A to 10V) from the data provided (TABLE 2).

Figure 10:
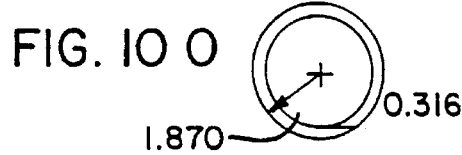
Figure 10P:
Figure 10Q:
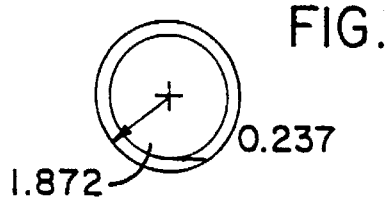
Figure 10R:
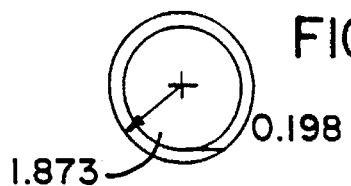
Figure 10S:
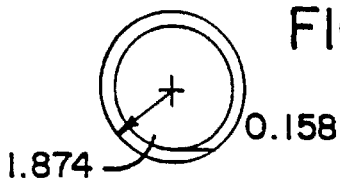
Figure 10T:
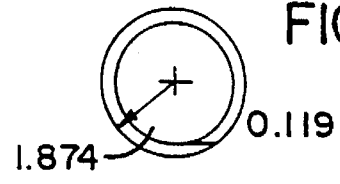
Figure 10U:
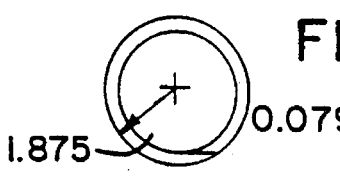
Figure 10V:
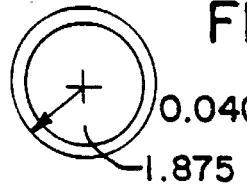

Under the conditions shown in FIG. 10 and TABLE 2, the spiroid would deliver 0.566 ml per rotation or 814 ml in one day with a rotation rate of 1 rpm. This finding clearly showed that gas and hydrostatic pressures within this defined spiroid would be balanced when the upper surface of the bore of the tubing was immersed 0.440" or 1.117 cm during rotation. At this depth of immersion, a hydrostatic pressure of 25.4 cm would be developed. The experimental data to follow is not contrary to these calculations. Rather it shows that these calculations rigorously define in a physical mechanical sense a point of exact gas and hydrostatic pressure balance in a spiroid.

Figure 10W:
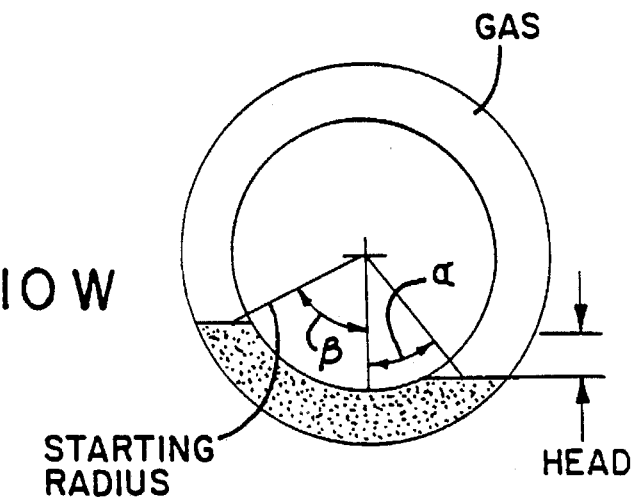

The radii estimated are paired with the terminal leg of the angle $\beta$ (FIG. 10W) converted to the rotational angle $\Theta$ having a value of zero at the discharge end of the spiroid. From this array of paired values the functional relationship of $\rho$ and $\Theta$ is established as is $d\rho/d\Theta$.

These values are thence used in the general integral for this type of planar geometric figure. The integrals are:

$$S_T = \int_{\Theta_{n-1}}^{\Theta_n} \left[ \rho^2 + \left( \frac{d\rho}{d\Theta} \right)^2 \right]^{1/2} d\Theta$$

$$S_L = \int_{\Theta_\alpha}^{\Theta_\beta} \left[ \rho^2 + \left( \frac{d\rho}{d\Theta} \right)^2 \right]^{1/2} d\Theta$$

Where $S_T$, is the total length of the coil along its center line; $S_L$, the length of the center line through the liquid in the coil; $\rho$, the radius scaler, $\Theta$, the angular orientation of the scaler in a polar frame of reference and $d\rho/d\Theta$ the differential of $\rho$ expressed as a function of $\Theta$.

The methods here advanced are recognized as proximate, but provide the basis for successive approximation to determine the geometry of the desired pressure balanced spiroid to any level of accuracy required. The assumption employed in determining $S_G$ from $S_T$ and $S_L$ (in general the coils were treated as if circular annuli) results in a slight proportional overestimation of $S_T$ and $S_L$ and a corresponding proportional overestimation of $S_G$. When the arduous reapproximation methods are invoked it is usually of no practical importance since the "corrections" availed by these methods are usually well within the most stringent manufacturing tolerances.

Figure 13A:
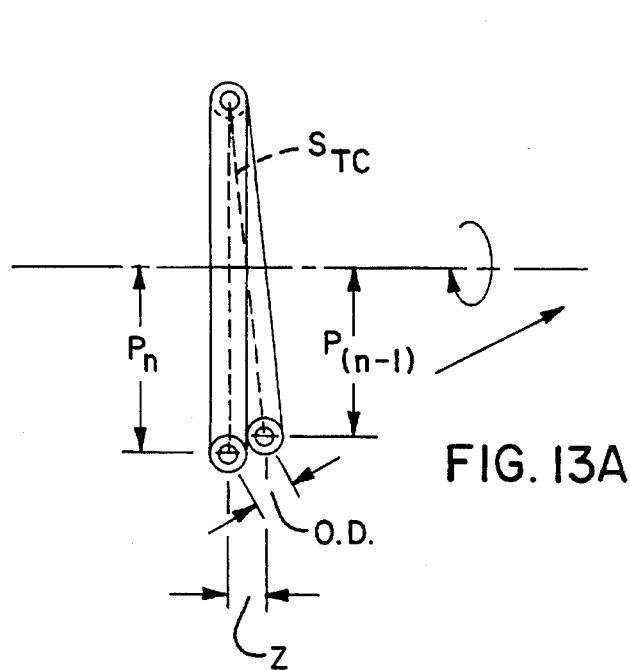
FIGS. 13A to 13C depict the method of determining the true length of the coils in a three dimensional spiroid such as the medium uptake spiroid.
Figure 13B:
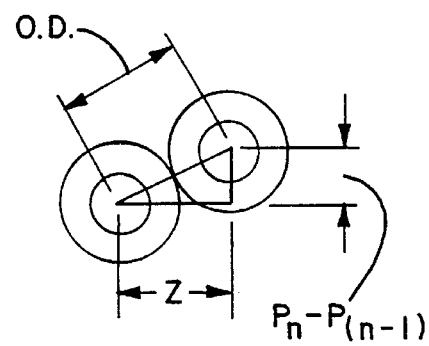
Figure 13C:
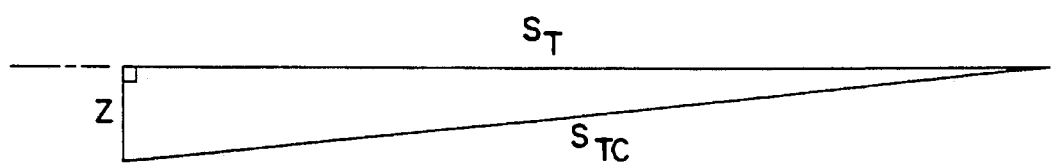

Within the $S_T$, $S_G$ and $S_L$ values calculated by the methods above resides a heretofore unaddressed source error of possible import. The lengths determined by integration are those of the center lines of the tubing coils ($S_T$) and center lines of the liquid pistons contained by it ($S_L$) as if in a spiral. The center lines of the successive coils of the tubing must be spaced so that they are no closer than the outside diameter of the tubing. To effect this correction, the integrated value of $S_T$ constitutes one leg of a right triangle (FIG. 13A to 13C). The value sought as the other leg must accommodate both the change in the radius vector in a planar polar coordinate system and movement of the radius vector's along the rotational axis of the spiroid.

The true length of a coil in the spiroid is defined by:

$$S_{TC} = \sqrt{(S_T)^2 + Z^2}$$

Where $S_{TC}$, is the true coil length, $S_T$, the coil length determined from integration of $\rho = f(\Theta)$ across a $2\Pi$ increment in a planar polar frame of reference and $$Z = \cos\left( \sin^{-1} \left( \frac{\rho_n - \rho_{(n-1)}}{O.D.} \right) \right) O.D.$$

Where Z, is the lateral displacement of the radius vector $\rho$ along the axis of rotation; O.D. the outside diameter of the tubing of which the spiroid is formed and $\rho_n$ and $\rho_{(n-1)}$ the radius vectors of the spiroid coil at the beginning and end of one rotation.

Where absolute rigor is required, the $S_{TC}$ value and $S_{LC}$ value similarly obtained using $\rho_\alpha$ and $\rho_\beta$ would be employed in the aforementioned reapproximations. The teaching of this method as distinct from the integration used for determination of $S_T$ and $S_L$ in the planar model was undertaken to more clearly elucidate the nature of the transformation from a planar polar coordinate system to a three dimensional system in which this sort of tubular spiroid truly resides. This correction using $\rho_\alpha$ and $\rho_\beta$ by appropriate methods may be incorporated into the $\rho = f\Theta$ formulae being integrated.

A source of inexactitude in calculating these radius vectors derives from determining the angle of deployment of $\beta$. When the length of the center line of the liquid piston, $S_{LC}$, is determined by the magnitude of $\beta$ and $\alpha$, in other than the discharge coil the value of $\alpha$ and $\beta$ is not solely a function of the hydrostatic head, the coil contributes to the total head. The $S_{LC}$ required for balance of pneumatic pressure and hydrostatic head in the discharge coil will exceed the $S_{LC}$ required to provide the required hydrostatic head for balance in the other coils of the spiroid. A portion of the liquid volume $S_{LC}$ represents lays in the bottom of the coil (See, FIG. 10W). In this position the liquid makes no contribution to the liquid head but does add to the magnitude of $\alpha$ and $\beta$ in all but the discharge coil.

It has been unequivocally shown that the point of balance between gas and hydrostatic pressures in a spiroid may be determined. This balanced condition does not necessarily define the limits of operation of the spiroid rather defines the submersion depth at which balance will occur and defines the geometry of a spiroid which will allow attainment of this balance at that submersion. A spiroid made with the dimensions provided (TABLE 2) is known to be adequately balanced for the purpose intended. Where amounts of submersion of the inlet coil during rotation is to be employed to change per rotation delivery rates a strict balance between hydrostatic and pneumatic pressures at widely different submersions of a fixed dimension spiroid is not possible.

The liquid piston in the small bore tubing moves as a liquid piston without gas escaping through or around it (FIG. 7A and 7B) so that the hydrostatic and attendant gas pressure differential can be increased due to the angular displacement of the intact liquid piston. An $S_{LC}$ 2.810290" generates a liquid head of about 0.87" when in position as diagrammed (FIG. 7A). This same $S_{LC}$ generates a liquid head of about 2.25" when displaced as diagrammed when in the discharge coil of the depicted feed spiroid (FIG. 9).

The effect of such displacement upon the generation of increased liquid heads and attendant increased gas pressure differential is proportionately greater with lower $S_{LC}$ values since the portion of $S_{LC}$ associated with the angle α which generates hydrostatic pressure in a displaced position is a greater proportion of the total $S_{LC}$.

The implications of this observation and the attendant results of such an intact displacement of the liquid pistons in small bore tubing is the basis for the unexpected hydrostatic head performance observed and reported below. The use of such liquid piston displacement in providing a range of "operative balance" between hydrostatic and gas pressures between the coils of the spiroids used is one of the many features of this invention separating it from all others. Designing spiroids that limit the liquid uptake volume of the inlet coil to less than the amount of liquid necessary to effect a maximum hydrostatic pressure in the discharge coil is vital for meaningful operation of the depicted bioreactor (FIG. 3).

Exact calculation of hydraulic and pneumatic pressures and recognition of the consequences of gas bubbling through and around the liquid pistons in response to imbalances between hydrostatic and pneumatic pressures are required if tubing with a substantially larger bore size is used and spiroids of this type are to be run out of balance. A large bore permits gas to bubble back through the liquid plug but a small bore does not. The "size" of large bore varies according to the viscosity of the liquid being pumped. For example, with a high viscosity liquid, a bore diameter of ¾ inch may not be a large bore but a ¾ inch diameter may be a large bore for a low viscosity liquid.

Figure 15:
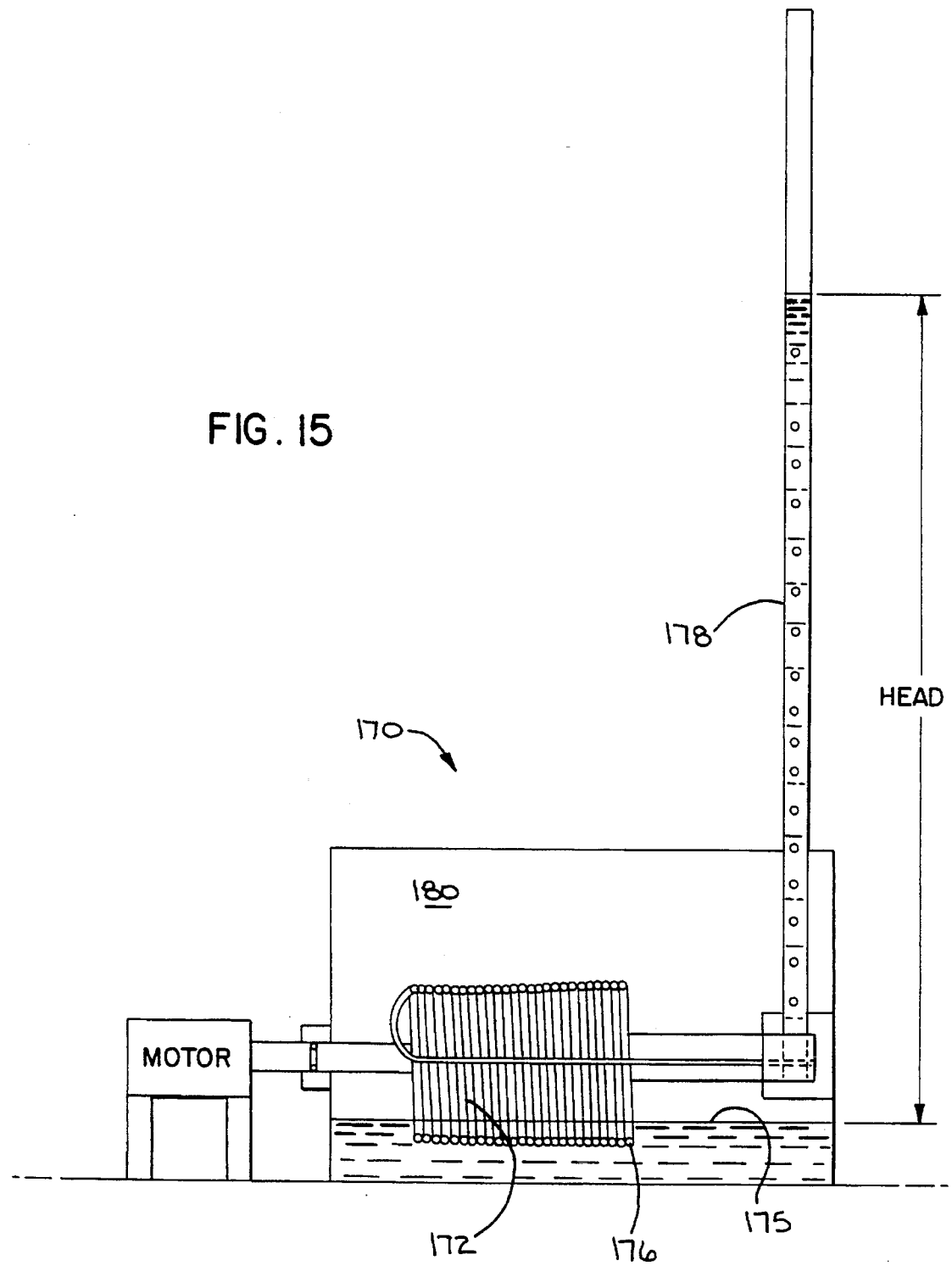
FIG. 15 depicts a hydrostatic head and per rotation flow rate determination device.

Using the equational relationship between ρ and Θ, a spiroid was formed by winding a 0.250 O.D., 0.125 I.D., silicone rubber tube around a precisely (±0.001") machined polycarbonate support. A hydrostatic pressure testing device 170, FIG. 15, was used to test the above described spiroid 172. Submersion was measured from the liquid phase surface 175 to the upper inside surface of the inlet 176 when it was most deeply submerged during rotation. Using water as a test liquid, it was found that the spiroid 172 would produce over 3.5 times the required minimum head requirement of 25.4 cm. when submerged at a depth which induced a per rotation delivery rate of 0.566 ml. per rotation. These empirical results showed the development of far greater hydrostatic heads than one would have previously expected. Operating at 0.5 rpm, the daily delivery rate can be halved or increased over 10 fold with no reduction in hydrostatic pressure.

It is doubtful if submersion less than the observed minimum submersion used for testing, 0.320 cm, would prove effective with this spiroid since this depth of immersion was required to induce flow of water into the tube opening. Other liquids may require greater submersion due to higher surface tensions and/or lower densities than water. The spiroid (FIG. 15, 172) behaves as expected with respect to per rotation delivery rates (FIG. 12) but exceed expected maximum pressure development particularly with low immersion. The highest hydrostatic head development, as would be expected, occurs when the spiroid is immersed to its axis of rotation, dropping off with deeper or lesser immersion.

The equation relating depth of immersion to pressure development expressed as liquid head is:

$$H = 45.711 + 45.2098I - 4.51194I^2 - 0.05970471I^3$$

Where: H is the liquid head in centimeters (cm.) and I is the maximum immersion of the inlet coil measured from the water surface to the upper side of the tubing bore.

Figure 11:
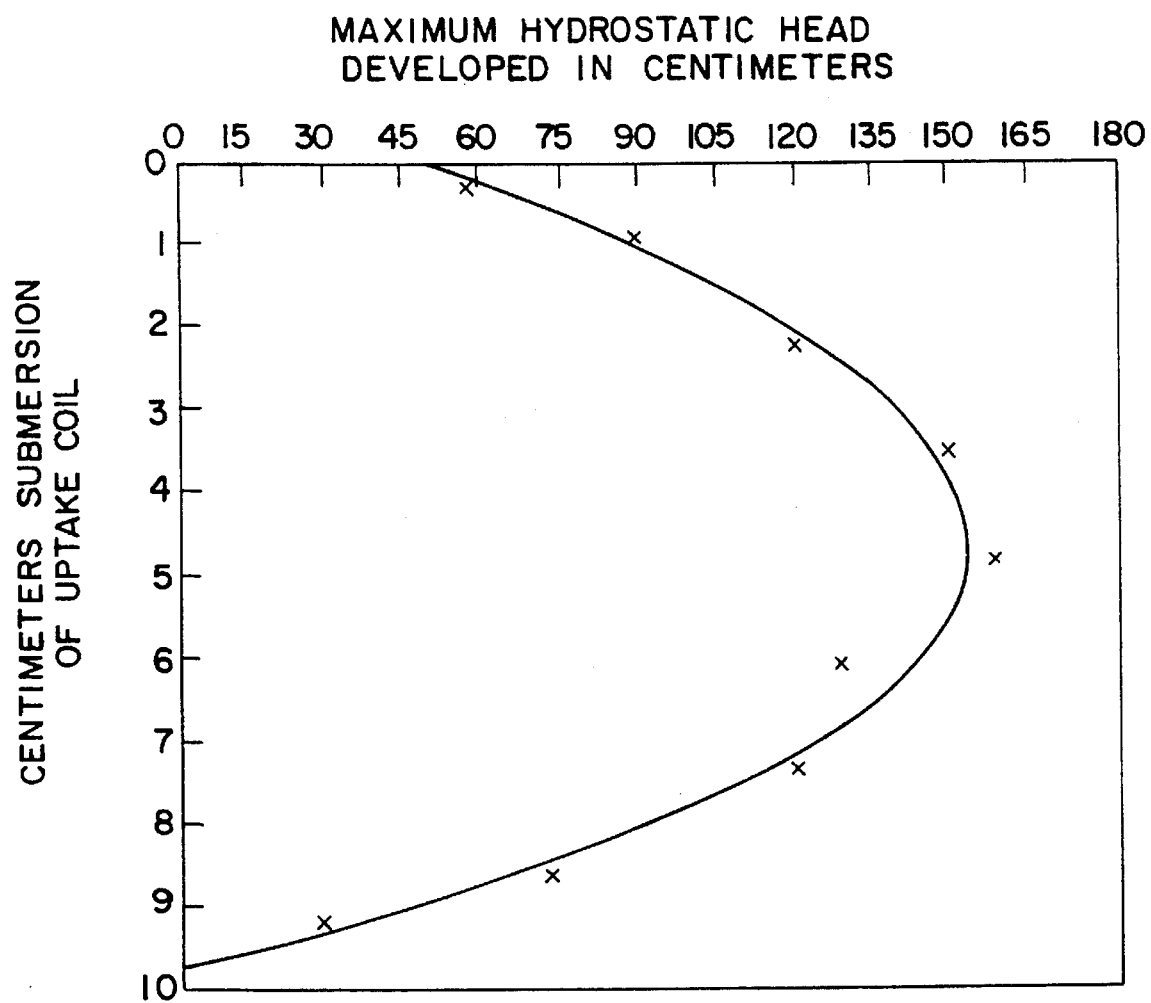
FIG. 11 shows the relationship of hydrostatic head development and depth of submersion during rotation of the designated medium uptake spiroid.
Figure 12:
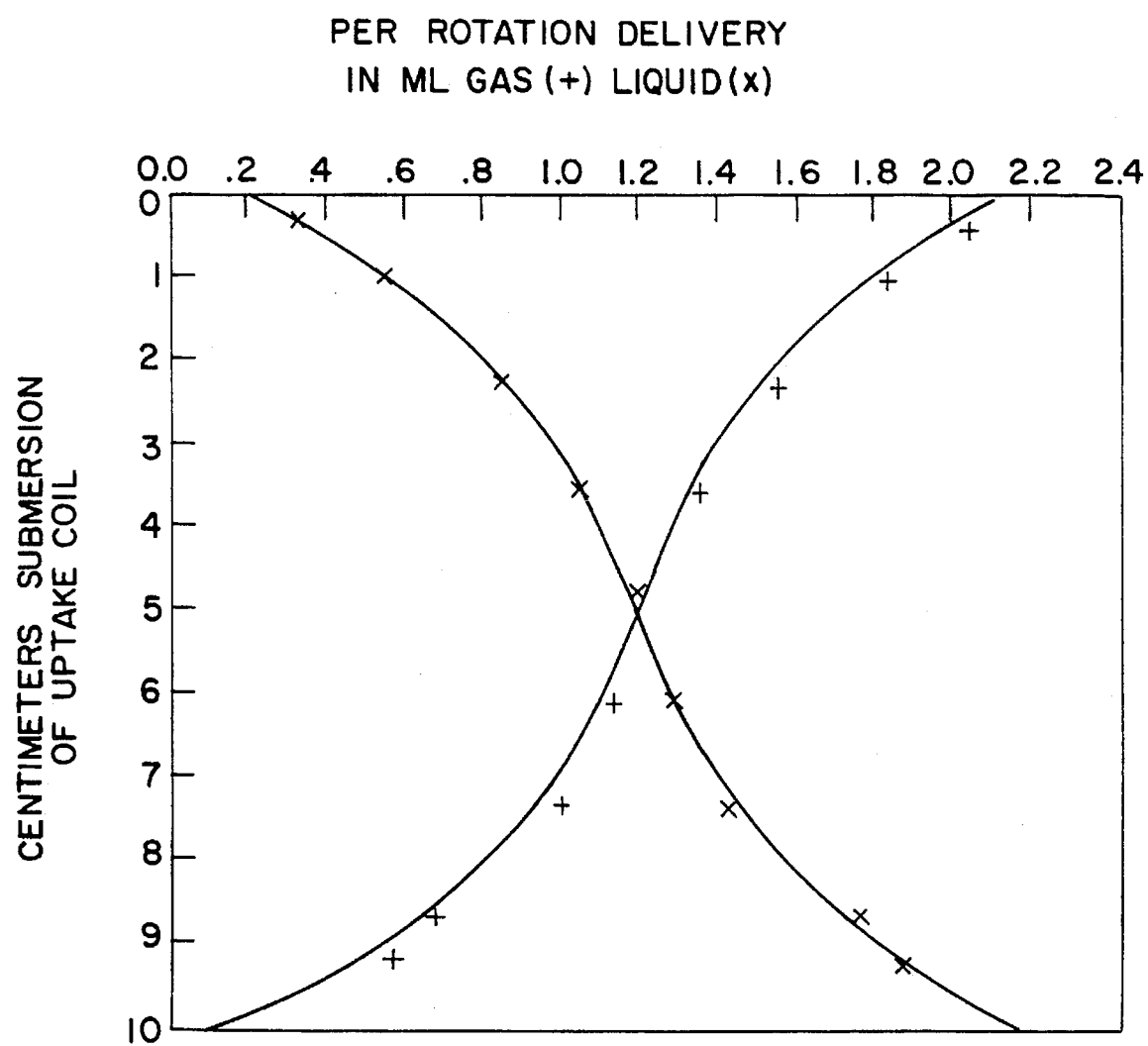
FIG. 12 shows the relationship of per rotation delivery rate of gas and liquid and depth of submersion during rotation of the designated medium uptake spiroid.
Figure 14:
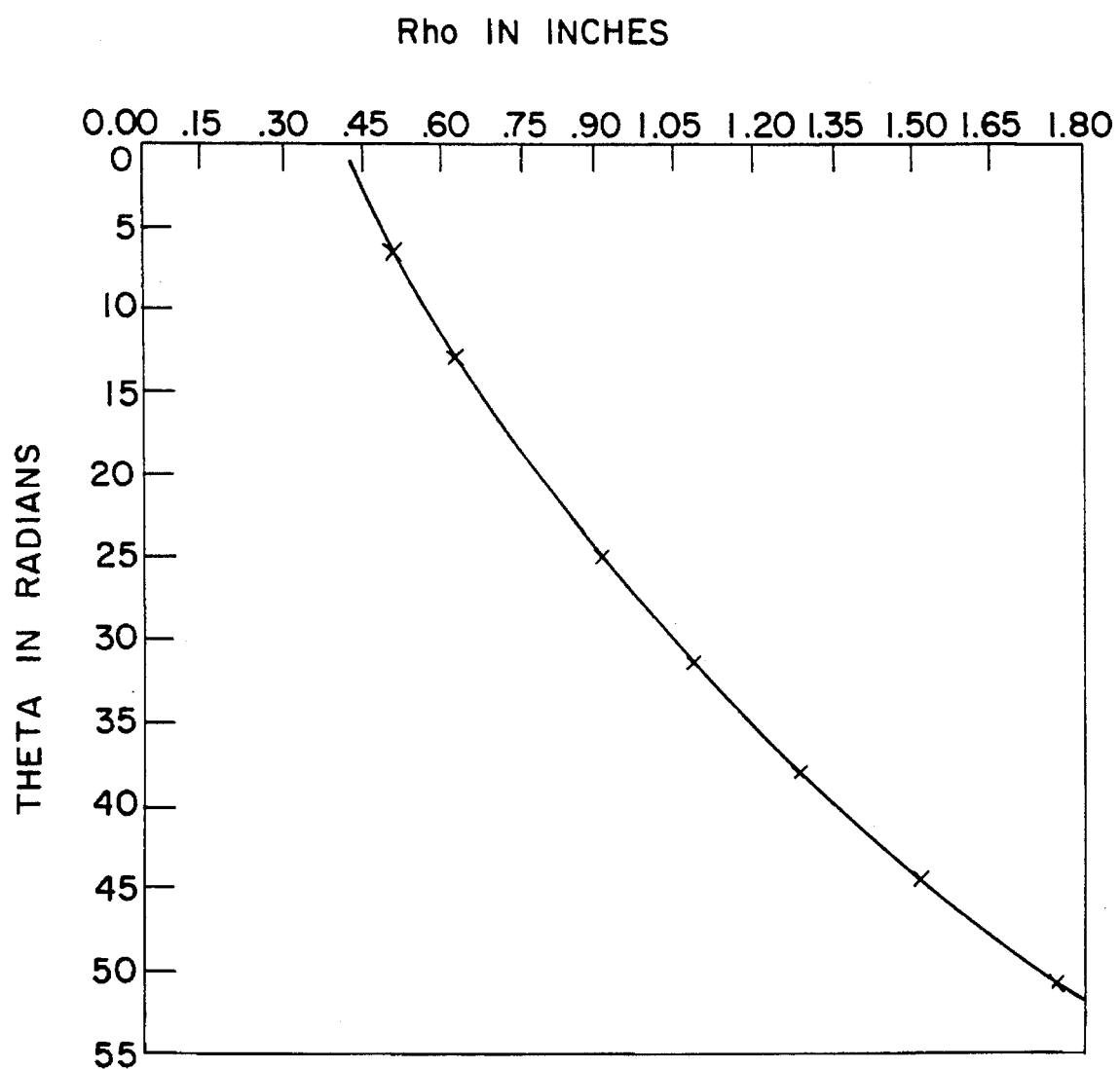
FIG. 14 shows the relationship between the angle of rotation and the distance from the origin of the center line of a close wound spiral tube used as an attachment insert spiroid.

This third degree equation and corresponding fitted curve minimizes the inherent vagaries in the empirical data and indicates a maximum hydrostatic pressure development at an immersion depth of the inlet coil of 4.599 cm. or to the axis of rotation of the spiroid (4.603 cm) (FIG. 11). Immersion of the inlet to this depth will develop about 152.4 cm. (60") of hydrostatic pressure which is equivalent to about 2.2 psi.

When the uptake coil of the spiroid is immersed to a depth of 1.117 cm producing a liquid piston 1.80" long (4.6 cm) a maximum hydrostatic head of 90.50 cm is generated. This is 3.56 times the expected delivery of 25.4 cm head when hydrostatic heads and pneumatic pressures are balanced. This result was wholly unexpected. Such outstanding performance is due to the observed and depicted intact displacement of the liquid pistons (FIG. 7A and 7B). Spiroids formed of sufficiently small bore tubing so that the entrapped gas can not escape from or rise through the liquid pistons will operate more effectively out of gas liquid balance than will those of such bore that the entrapped gas may escape.

Observed spiroid delivery of fluid at this 1.117 cm immersion depth is 0.588 ml per rotation or 846 ml in one day with a rotation rate of 1 rpm. The calculated delivery rate of 0.565 ml per rotation and 814 ml per day delivery with a rotation rate of 1 rpm, is in close agreement with the observed.

The design of spiroids which will attain gas liquid balance at low per rotation delivery rates and will, due to intact liquid piston displacement generate above expected levels of pressure is one outstanding feature of this invention.

When the defined hydrostatic head for a given submersion is exceeded (FIG. 11), liquid back flow from the hydrostatic column 178 (FIG. 15) through the spiroid 172 and back into the reservoir 180 occurs. Once this back flow is initiated, the spiroid acts as a simple siphon and the hydrostatic column 178 drains until empty. The spiroid 172 does not quickly recover unless purged with gas to remove randomly distributed liquid pistons in the coils which form when the siphon is broken.

This strongly cites against the use of this spiroid at or near the hydrostatic pressure limit for a given immersion. Since the spiroid designed and tested consistently operated well above the prescribed pressure constraint, 10" or 25.4 cm. of liquid head except when submerged beyond 9.2 cm. depth, it is satisfactory for use as predicated. At any pressure submersion configuration, less than the maximum attainable with that submersion, rotation may be stopped with no back flow, the liquid pistons in the coil remain in place and collectively act as a hydraulic "foot valve".

The per rotation rate of liquid and gas delivery (FIG. 12) as a function of depth of immersion are defined by $V_L=0.200+0.4149I-0.065598I^2+0.00435089I^3$ and $V_G=2.174-0.4149I+0.065598I^2+0.00435089I^3$ Where $V_L$ and $V_G$ are the milliliters delivered per rotation and I is the maximum immersion of the inlet measured from the water surface to the upper side of the tubing bore opening at deepest submersion.

Liquid delivery is inexorably linked to gas delivery whenever immersion is sufficient to form a liquid seal in the spiroid thus each rotation delivers both liquid and gas to the reaction vessel. Using this spiroid and a minimum liquid delivery configuration (about 3.2/mm. submersion) with a 0.5 rpm rotation rate, a daily liquid delivery of 235 ml. per day along with 1,474 ml. of gas is realized. Operating at 10 rpm with a submersion of 9.2 cm. for maximum liquid delivery, a daily liquid delivery of 26,762 ml. would be accompanied by a gas delivery of 7,423 ml.

Liquid delivery can be increased by increasing both the rotation rate and immersion to obtain an output from a low of 235 ml. per day to about 114 times that amount. At a constant rotation rate, the increase attainable from immersion depth change alone over the 0.32 through 9.21 cm. range is on the order of 5.7 fold.

Neither pressure nor rotation rate in the defined operative ranges will affect per rotation delivery of liquid and gas from the spiroid depicted.

Attention was focused upon gas liquid pressure balancing with full knowledge that, as applied, transgressions upon this balance would be commonplace. Using the physical mechanics based approximations for construction of the medium uptake spiroid, the permissible limits of these transgressions were assessed. It was unexpectedly found that the spiroid performed exceedingly well beyond expected limits of performance with respect to pressure development. No rigorous empirical proof is advanced that this spiroids's exact geometric configuration is outstandingly better than other modified spiroids of the same general design. It is clear, however, that this particular spiroid is adequate for its intended use and in this specific form is provided as an example of a preferred embodiment for the feed spiroid.

EXAMPLE 2: DESIGN OF A SURFACE INCREASING INSERT FOR GROWING ATTACHMENT DEPENDENT CELL IN A REACTION VESSEL

When a uniform bore spiroidal insert is used within the reaction vessel, the angular velocity of a point midway between the surface of the insert decreases with the distance from the axis of rotation. The rate of liquid flow through an aperture is in general accord with the aperture cross-sectional area. Addressing these two conditions can be accomplished by constructing an insert spiroid such that the ratio of $\rho$ and the inside cross-sectional dimension along the length of the insert spiroid (the "rectangular tubing") is constant:

$$\rho/2\Delta r=K$$

Where: $\rho$ is the radius vector of the spiroid; $\Delta r$ is one half the radius opening of the tubing after rotation of the radius vector, $\rho$, through the angle $\Theta$; and K is a constant for any $\rho$ and $\Theta$.

The above equational statement is applied in practice directly by noting that the spiroid to be used is an insert, thus the greatest value of $\rho$ is the radius of the cylinder less one half the initial radial dimension of the single walled rectangular tubing of which the insert is to be formed. In the depicted spiroidal insert (FIG. 6), the greatest value of $\rho$ equals 1.875"–0.125" since the initial radial opening dimension is stipulated as 0.250" and the inside radius of the cylinder 1.875". The curving portions of the spiroid are formed of material with a wall thickness (WT) of 0.03125.

The value of K can be determined based upon a known $R_n$ and $2\Delta r_n$ as:

$$\frac{R_n}{2\Delta rn} = K \text{ or in the depicted spiroid } \frac{1.875 - 0.125}{0.250} = 7$$

$$\text{Since } \frac{R_n}{2\Delta rn} = \frac{R_{n-1}}{2\Delta r(n-1)} = K$$

$$\frac{R(n-1)}{R_n} = \frac{\Delta r(n-1)}{\Delta rn} \text{ and since}$$

$$R(n-1) = R_n - \Delta rn - (WT) - \Delta r(n-1)$$

By Substitution:

$$\Delta r(n-1) = \frac{\Delta rn(R_n - \Delta rn - WT)}{R_n + \Delta rn}$$

or in the depicted spirod
$\Delta r(n-1) = 0.106250 \ 2\Delta rn - 1 = 0.2125$
$R_{n-1} = 1.4875$ and in the depicted spirod $$\frac{1.4875}{0.2125} = 7$$

Appropriate value for $\rho$ and $\Delta r$ for all lower number coil can be determined by recursive use of this approach.

What has been done when this is completed is the values for $\rho$ in the depicted spiroid have been established for $\Theta$ at 0, 2Π, 4Π, . . . 2nΠ. When this is done an appropriate equation relating $\rho$ and $\Theta$ may be determined.

When the functional relationship of the values of $\rho$ and $\Theta$ so determined is tested the polynomial: $\rho=4.078891 \cdot 10^{-1}+1.424026 \cdot 10^{-2}\Theta+1.676033 \cdot 10^{-4}\Theta^2+9.608163 \cdot 10^{-7}\Theta^3+1.265811 \cdot 10^{-8}\Theta^4$ is virtually a perfect fit to the data (FIG. 14) and defines the functional relationship of $\rho$ and $\Theta$. The equation yields a integrand from which the length of the centerline of the spiroid (TABLE 3) may be determined. The integrand for this specific insert is:

$$S = \int_{\theta_1}^{\theta_2} \sqrt{\begin{array}{l}1.6731 \cdot 10^{-1} + 1.165207 \cdot 10^{-2}\theta + 3.4001 \cdot 10^{-4}\theta^2 + \\ 5.5623 \cdot 10^{-6}\theta^3 + 6.5847 \cdot 10^{-8}\theta^4 + 6.8287 \cdot 10^{-10}\theta^5 + \\ 5.1688 \cdot 10^{-12}\theta^6 + 2.4325 \cdot 10^{-14}\theta^7 + 1.6023 \cdot 10^{-16}\theta^8 \end{array}}$$

which is the expanded form of:

$$S = \int \sqrt{\rho^2 + \frac{d\rho}{d\theta}} \, d\theta$$

The spiroid is formed to these dimensions from a sheet of 1/32" polycarbonate about 24" wide and 48" long yielding a growth area of about 2,300 sq. in. or 14,900 sq. cm. The curved cylinder surface of 295 sq. in. or 1900 sq. cm. is not lost as a growth surface rather provides additional growth surface. In total this 24" long reaction chamber with the insert described will provide 16,800 sq. cm. of surface for cell growth, an increase of over 7.8 fold in surface area available for attachment dependent cell growth.

This insert spiroid (FIG. 6 and TABLE 3) operates against no overall hydrostatic pressure for it discharges directly into the reaction chamber which is this spiroid's uptake reservoir. Out of balance gas pressures are however developed within the spiroid, due to the decreasing radial cross section and decreasing radius of successive coils.

TABLE 3

Various parameters of a constant surface flow spiroid at 180. intervals. Volumes presented do not include a constant axis length multiplier.

| Coil # | Angle of Rotation | Radius, ρ | Δr* | Length | Volume ml** | H max*** |
|---|---|---|---|---|---|---|
|  | 0 | 0.4079 | 0.0291 |  |  |  |
|  |  |  |  | 1.3571 | 32.878 | 0.8006 |
| 1 | 180 | 0.4543 | 0.0325 |  |  |  |
|  |  |  |  | 1.5084 | 40.637 | 0.8901 |
|  | 360 | 0.5043 | 0.0360 |  |  |  |
|  |  |  |  | 1.6711 | 50.060 | 0.9863 |
| 2 | 540 | 0.5579 | 0.0399 |  |  |  |
|  |  |  |  | 1.8458 | 60.906 | 1.0895 |
|  | 720 | 0.6155 | 0.0440 |  |  |  |
|  |  |  |  | 2.0386 | 73.901 | 1.2005 |
| 3 | 900 | 0.6774 | 0.0484 |  |  |  |
|  |  |  |  | 2.252 | 93.899 | 1.3198 |
|  | 1080 | 0.7439 | 0.0531 |  |  |  |
|  |  |  |  | 2.4517 | 107.555 | 1.4479 |
| 4 | 1260 | 0.8153 | 0.0582 |  |  |  |
|  |  |  |  | 2.6842 | 128.686 | 1.5854 |
|  | 1440 | 0.8920 | 0.0637 |  |  |  |
|  |  |  |  | 2.9339 | 153.811 | 1.7330 |
| 5 | 1620 | 0.9743 | 0.0696 |  |  |  |
|  |  |  |  | 3.2023 | 183.247 | 1.8916 |
|  | 1800 | 1.0628 | 0.0759 |  |  |  |
|  |  |  |  | 3.4905 | 217.722 | 2.0621 |
| 6 | 1980 | 1.1579 | 0.0827 |  |  |  |
|  |  |  |  | 3.8002 | 258.114 | 2.2452 |
|  | 2160 | 1.2600 | 0.0900 |  |  |  |
|  |  |  |  | 4.1329 | 305.255 | 244.19 |
| 7 | 2340 | 1.3697 | 0.0978 |  |  |  |
|  |  |  |  | 4.4903 | 360.438 | 2.6524 |
|  | 2520 | 1.4875 | 0.1063 |  |  |  |
|  |  |  |  | 4.8742 | 424.801 | 2.9700 |
| 8 | 2700 | 1.6141 | 0.1153 |  |  |  |
|  |  |  |  | 5.2863 | 499.595 | 3.1283 |
|  | 2880 | 1.7500 | 0.1250 |  |  |  |
|  |  |  |  | 47.9979 |  |  |

*Δr is one half the radial distance between the walls of the spiroid at the stated amount of rotation.
**Volume for the half coil presumes a spiroid 24 inches in length along its axis.
***H max is the maximum hydrostatic pressure in inches the defined half coil of the spiroid will support EXAMPLE 3: DESIGN OF A SURFACE INCREASING INSERT FOR GROWING SUSPENDED CELLS IN A REACTION VESSEL If the reactor is to be used with suspended cell cultures there is no need to maintain a constant rate of movement of the liquid phase with respect to the walls of the insert, for the cells are not attached to the insert walls; rather, they are suspended in the liquid and move with it. When the culture is of suspended cells, tissues, or other cell aggregates, tapered bore spiroids are disadvantageous. Suspended cells, tissues or cell aggregates which will not pass through the discharge opening of the spiroid may enter the uptake opening of the tapered spiroid and thus block the spiroid.

With suspension cultures, spirals made of uniform bore tubing may be advantageously used as a bioreactor tube insert 182 (FIG. 16C). In a bioreactor, such inserts 182 will increase surface area for adsorption and absorption of gases from the reactor atmosphere into the liquid and further will decrease the path of diffusion of the absorbed gas to the organism. By this same reasoning, biologically produced gases will be more easily released to the atmosphere.

The locus of the center line of the bore of a tightly wound tubular spiral insert 182 made of ¼" O.D.×⅛" I.D. tubing with a 1" diameter passage along its central discharge to accommodate necessary bioreactor tubes and elements (which are shown in FIG. 3—gas tube 110, recirculation element 34B and feed element 66B) and which will fit within a 3¾" I.D. cylindrical chamber may be described by the general form $\rho=a+k\Theta$. Where ρ is the radius vector in a polar frame of reference; a, the value ρ; where Θ, the angle of rotation of the radius vector, equals zero and k, the coefficient of Θ. (The coefficient is determined as O.D./2Π if the spiral is tightly wound.)

Substituting the above parameters, the above equation is $\rho=0.500+3.978874 \cdot 10^{-2}\Theta$ when Θ is in radians then $d\rho/d\Theta=3.978874 \cdot 10^{-3}$.

The length of the centerline of the tubing of which this spiral is made is described generally by:

$$S = \int_{\Theta_o}^{\Theta_n} \left[\rho^2 + \left(\frac{d\rho}{d\Theta}\right)^2\right]^{1/2} d\Theta$$

or with substitution of constants by $$S = \int_{\Theta_o}^{\Theta_n} [0.251583 + 3.978874 \cdot 10^{-2}\Theta + 1.153144 \cdot 10^{-3}\Theta^2]^{1/2} d\Theta$$

Since this spiral includes 5.5 coils the limits of this definite integral are Θ=0 and Θ=34.557519 radians, with these limits of integration S=41.063 inches. The internal (16.125 sq.in.) and external (32.251 sq.in.) surface area of a tube 41.063 inches long and 0.125 I.D. and 0.2500 O.D. is 48.376 sq. in. About 90–94 spirals of ¼ O.D. tubing may be easily inserted in a 24 inch long reaction chamber with ample space for liquid return to the liquid pool in the bottom of the horizontally deployed bioreactor chamber (FIG. 16C). Uniformity of flow from the spirals during rotation is assured by appropriately staggering their uptake and discharge ends around the axis of rotation.

The surface area added by these tubular spiral inserts, assuming 90 spirals are used, equals 4353.84 sq. inches. The area of the cylinder wall in this vessel is 282.74 sq. inches. Thus, the total surface area of the vessel with the 90 tubular spiral inserts is increased from 282.74 sq. inches to 4353.83 sq. inches or by about 15.4 fold.

The maximum distance from the inner wall to the tubing centerline is 0.0625 inches. The spiral cavity between closely packed adjacent spirals, (FIGS. 16A to 16D), forms a second set of spirals. This spiral has a cross-sectional area of 0.013413 sq. inches as contrasted to 0.012272 sq. inches cross-sectional area of the ⅛" bore tubing. The ratio of internal wall surface to cross-section in the tubing bore is about 32:1. In the spiral cavity formed between coils of adjacent spirals this ratio is about 58.6:1. This spiral between adjacent spirals is of significant importance.

This type of bioreactor is well suited for the culture of numerous plant, animal, bacterial or fungal cells or plant or animal tissues or fungal mycelial mats or bacterial aggregates whether attachment dependent or cultured in suspension.

This type of reactor will handle any sort of liquid medium which will flow through a tube.

This type of reactor will operate with any gas and can operate effectively under substantially elevated gas pressures or vacuums.

The above described advantages derive from the structure of the reactor. The placement of the recirculation spiroid within the reaction chamber insures mixing of both gases and liquids within the reaction chamber assuring a uniform environment therein. The feed spiroid permits gas and liquid phases to be introduced into the reaction chamber at a precisely controlled rate and without jeopardizing sterility within the reaction chamber. The enhanced mixing insures that the constantly added gas and liquid will be readily mixed to obtain uniformity. Sampling and monitoring of reactor contents is achieved by providing a section of the recirculation spiroid and extending to the exterior of the reaction vessel. Spiroids rotate with the reaction vessel minimizing the number of moving parts and simplifying the construction of the reactor and making it more durable and trouble-free. Reactor contents including cells and tissues are subjected to minimal shear forces because the preferred reaction vessel is cylindrical and all spiroids have a smooth walled lumen. Cells are not damaged by mixing which enhances cell propagation and production. Increased viscosity of liquid within wide ranges has little effect on the mixing system. The insert spiroid increases the surface area within the reaction chamber which is particularly useful for attachment of dependant cells and catalysts. The feed spiroid preferably has coils that are of uniform bore but are successively smaller in coil diameter from the inlet to the discharge coil which effects gas and liquid pressure balance and thus prevents gas back flow and permits the generation of greater hydrostatic pressure in a spiroid having a large bore lumen.

The reactor is particularly well suited for use as a bioreactor for the culture of cells. The nutrient level within the reaction chamber is maintained at an optimum level throughout the reaction chamber by mixing. Fresh nutrients contained in the liquid and fresh gas are introduced into the reaction chamber at a controlled constant rate to maintain the optimal nutrient and dissolved gas level without jeopardizing sterility within the reaction chamber. Furthermore, the nutrient level and gas input within the reaction chamber can be adjusted to meet the changing aeration and nutrient levels for the cells or tissues as they go through their various stages of growth and development.

I claim:

1. A reactor capable of maintaining a controlled environment in a reaction vessel to facilitate a reaction, the reactor comprising:

a rotatable reaction vessel defining a reaction chamber capable of holding a gas phase reactant and a liquid phase reactant; and a spiroid having successive coils operably associated with the reaction chamber, the spiroid also being operably associated with the reaction vessel so that rotation of the reaction vessel causes rotation of the spiroid and movement of gas phase reactant in the reaction chamber through the spiroid, the spiroid having an upstream direction extending from an outlet to an inlet with each successive coil having a volume less than the volume of the upstream coil.

2. The reactor of claim 1 wherein at least one of the inlet and outlet is within the reaction chamber.

3. The reactor of claim 1 wherein the reaction vessel defines first and second chambers in fluid and gaseous communication with each other, the cross-sectional area, taken perpendicular to the axis about which the reaction vessel rotates, of the first chamber being greater than that of the second chamber, the spiroid having at least one coil in the first chamber.

4. The reactor of claim 1 wherein the spiroid is associated with the reaction vessel so that rotation of the reaction vessel causes liquid phase reactant in the reaction chamber to pass through the spiroid.

5. The reactor of claim 1 further comprising:

a feed reservoir vessel capable of holding additional reactant; and a feed spiroid having an inlet and an outlet, the inlet being positioned in the reservoir vessel and the outlet being positioned in the reaction chamber.

6. The reactor of claim 5 wherein the reservoir vessel is a stationary reservoir vessel and the feed spiroid is associated with the reaction vessel so that rotation of the reaction vessel causes rotation of the feed spiroid.

7. The reactor of claim 5 further comprising means for controlling the depth of immersion of the inlet in the additional reactant in the reservoir vessel.

8. The reactor of claim 5 further comprising means for controlling the rate of rotation of the inlet through the additional reactant in the reservoir vessel.

9. The reactor of claim 5, further comprising a standpipe to control the level of liquid phase reactant in the reactor chamber, the standpipe generating a hydrostatic pressure, the feed spiroid being in fluid communication with the standpipe and developing a pressure capable of overcoming the hydrostatic pressure.

10. The reactor of claim 1 further comprising a discharge, the discharge being operably associated with the reaction vessel and reaction chamber so that rotation of the reaction vessel causes reactant to be removed from the reaction chamber through the discharge.

11. The reactor of claim 1 further wherein the reaction vessel has therein contents that includes the reactant and further comprising means for sampling the contents of the reaction chamber, the sampling means comprising a sampling spiroid capable of transporting the contents from the reaction chamber to the exterior of the reaction chamber.

12. The reactor of claim 11 wherein the sampling spiroid is capable of transporting the contents back into the reaction vessel.

13. The reactor of claim 11 wherein the sampling spiroid is operably associated with the reaction vessel and reaction chamber so that rotation of the reaction vessel causes reactant to be removed from the reaction chamber through the sampling spiroid.

14. The reactor of claim 1 further comprising:

a stationary feed reservoir vessel and a feed spiroid having an inlet and an outlet, the inlet being positioned in the reservoir vessel and the outlet being positioned in the reaction chamber, the feed spiroid being associated with the reaction vessel so that rotation of the reaction vessel causes rotation of the feed spiroid, the reservoir vessel being capable of holding a reactant at a level;

a discharge being operably associated with the reaction vessel and reaction chamber so that rotation of the reaction vessel causes liquid to be removed from the reaction chamber through the discharge; and means for sampling the liquid of the reaction chamber, the sampling means comprising a sampling spiroid capable of transporting the reactant from the reaction chamber to the exterior of the reaction chamber, the sampling spiroid being operably associated with the reaction vessel so that rotation of the reaction vessel causes the sampling spiroid to transport the reactant of the reaction chamber.

15. The reactor of claim 14 further comprising means for controlling the reactant level in the feed reservoir vessel.

16. The reactor of claim 15 wherein the controlling means comprises a sight glass in fluid communication with the feed reservoir vessel, and a photoelectric eye that senses a meniscus of the reactant in the sight glass.

17. The reactor of claim 1 further comprising a feed reservoir vessel and a feed spiroid having (1) coils made of tubing, one of the coils being an inlet coil and another coil being a discharge coil, (2) an inlet of the inlet coil and (3) an outlet on the discharge coil, the inlet being positioned in the reservoir vessel and the outlet being positioned in the reaction chamber, the minimum number of coils (N) for the feed spiroid having a stipulated total liquid head ($H_t$), assuming that the change in head ($\Delta h$) between each successive coil is held uniform, is determined by $$2(R_1-r)=Q(2H_t/N+1),$$

where $R_1$ is the radius of the centerline of the tubing of the discharge coil; r is the inner radius of the tubing; $H_t$ is the stipulated total liquid head the feed spiroid is to deliver; N the minimum number of coils of the feed spiroid; Q is the reciprocal of the fraction of the maximum head ($2(R_1-r)$) the discharge coil can reach when the feed spiroid is balanced with respect to hydrostatic and pneumatic pressures.

18. The reactor of claim 1 further including a standpipe to control the level of liquid in the reaction vessel.

19. The reactor of claim 1 further comprising a surface increasing insert capable of being received in the reaction chamber.

20. The reactor of claim 19 wherein the insert is made of tubing and the tubing is of non-uniform bore.

21. The reactor of claim 19 wherein the insert comprises uniform bore tubing.

22. A reactor capable of containing a reactant, the reactor comprising:
rotatable means for containing the reactant; and
means for recirculating the reactant within the containing means, the recirculating means being at least partially within, and being operably associated with, the containing means so that rotation of the containing means causes the recirculating means to recirculate the reactant.

23. The reactor of claim 22 further comprising:
means for storing additional reactant to be supplied to the containing means; and
rotatable means for transferring additional reactant from the storing means to the containing means.

24. The reactor of claim 23 wherein the reactant storing means is a stationary reactant storing means and the transferring means is associated with the rotatable containing means so that rotation of the containing means causes rotation of the transferring means and transfer of the additional reactant.

25. The reactor of claim 23 further comprising means for controlling the reactant level in the containing means, the controlling means generating a hydrostatic pressure, the transferring means being in fluid communication with the controlling means and being able to overcome the hydrostatic pressure.

26. The reactor of claim 22 further comprising means for sampling the contents of the containing means, the sampling means being capable of transporting the reactant from the containing means to the exterior of the containing means.

27. The reactor of claim 26 wherein the sampling means is capable of transporting the reactant back into the containing means.

28. The reactor of claim 26 wherein the sampling means is a sampling spiroid operably associated with the containing means so that rotation of the containing means causes the sampling spiroid to transport the reactant from the containing means.

29. The reactor of claim 22 further comprising:
means for storing additional reactant to be supplied to the containing means;
rotatable means for transferring the additional reactant from the storing means to the containing means, the transferring means being associated with the containing means so that rotation of the containing means causes rotation of the transferring means; and
means for sampling the reactant of the containing means, the sampling means comprising a sampling spiroid capable of transporting the reactant from the containing means to the exterior thereof, the sampling spiroid is operably associated with the containing means so that rotation of the containing means causes the sampling spiroid to transport the reactant from the containing means.

30. The reactor of claim 22 further comprising: means for storing reactant to be supplied to the containing means; and
rotatable means for transferring the reactant from the storing means to the containing means, the transferring means being associated with the containing means so that rotation of the containing means causes rotation of the transferring means, the transferring means having (1) coils made of tubing, one of the coils being an inlet coil and another coil being a discharge coil, (2) an inlet on the inlet coil and (3) an outlet on the discharge coil, the inlet being positioned in the storing means and the outlet being positioned in the containing means, the minimum number of coils (N) for the transferring means having a minimum total liquid head ($H_t$), assuming that the change in head ($\Delta h$) between each successive coil is held uniform, is determined by:

$$2(R_1-r)=Q(2H_t/N+1)$$

where $R_1$ is the radius of the centerline of the tubing of the discharge coil; r is the inner radius of the tubing; $H_t$ is the minimum total liquid head the transferring means is to deliver; N is the minimum number of coils of the transferring means; and, Q is the reciprocal of the fraction of the maximum head ($2(R_1-r)$) the discharge coil can reach when the transferring means is balanced with respect to hydrostatic and pneumatic pressures.

31. The reactor of claim 22 further comprising means for increasing the surface area within the containing means.

32. A method of performing a reaction using a reactor having a rotatable reaction vessel defining a reaction chamber capable of holding a reactant, the reaction chamber having a spiroid therein that is operably associated with the reaction vessel so that rotation of the reaction vessel causes rotation of the spiroid and movement of the reactant through the spiroid, the method comprising the steps of:
introducing reactant into the reaction chamber; and
rotating the reaction vessel.

33. The method of claim 32 wherein the reactor has a feed spiroid having an outlet in the reaction chamber and an inlet, the feed spiroid being operably associated with the reaction vessel so that rotation of the reaction vessel causes rotation of the feed spiroid, the method further comprising the step of transporting additional reactant through the feed spiroid into the reaction chamber.

34. The method of claim 33 wherein the reactor has a feed reservoir vessel capable of holding additional reactant, the inlet of the feed spiroid being in the reservoir vessel, the method further comprising the step of adjusting the depth of immersion of the inlet in the additional reactant to adjust the rate at which the additional reactant is introduced into the reaction chamber.

35. The method of claim 33 wherein the reactor has a feed reservoir vessel capable of holding additional reactant, the inlet of the feed spiroid being in the reservoir vessel, the method further comprising the step of adjusting the rate of rotation of the inlet in the additional reactant to adjust the rate at which the additional reactant is introduced into the reaction chamber.

36. The method of claim 34 wherein the adjusting step includes the step of controlling the level of additional reactant in the reservoir vessel.

37. The method of claim 32 wherein the reactor has means for controlling the reactant level in the reaction chamber, the controlling means generating a hydrostatic pressure, the spiroid being in fluid communication with the controlling means, the method further comprising the step of overcoming the hydrostatic pressure with the spiroid.

38. The method of claim 32 wherein the reactor has a discharge, the discharge being operably associated with the reaction chamber so that rotation of the reaction vessel causes reactant to be removed from the reaction chamber through the discharge, the method further comprising the step of removing reactant from the reaction chamber through the discharge.

39. The method of claim 32 wherein the reactor has a sampling spiroid operably associated with the reaction vessel so that rotation of the reaction vessel causes rotation of the sampling spiroid and movement of the reactant therethrough, the method further comprising the step of sampling the reactant in the reaction chamber using the sampling spiroid.

40. The method of claim 32 further comprising the step of inserting a means for increasing the surface area in the reaction chamber into the reactor chamber.

41. A reactor capable of maintaining a controlled environment in a reaction vessel to facilitate a reaction, the reactor comprising:

a rotatable reaction vessel defining a reaction chamber capable of holding a reactant; and a feed spiroid for transferring liquid phase and gas phase reactants into the reaction chamber, the feed spiroid having (1) successive coils made of tubing, one of the coils being an inlet coil and another coil being a discharge coil, with each coil having a volume less than the volume of the successive coil disposed closer to the inlet coil, (2) an inlet in the inlet coil and an outlet in the discharge coil, the outlet being positioned in the reaction chamber, the minimum number of coils (N) for the feed spiroid having a minimum total liquid head ($H_t$), assuming that the change in head ($\Delta h$) between each successive coil is held uniform, being determined by:

$$2(R_1-r)=Q((2H_t)/(N+1)),$$

where $R_1$ is the radius of the centerline of the tubing of the inlet coil, r is the inner radius of the tubing and Q is the reciprocal of the fraction of the approximate maximum head ($2(R_1-r)$) the discharge coil can reach when the spiroid is balanced with respect to hydrostatic and pneumatic pressures, the spiroid being configured so that rotation of the spiroid generates an increase in pressure from the inlet coil to the discharge coil.

42. The reactor of claim 41 wherein the feed spiroid is operably associated with the reaction vessel so that rotation of the reaction vessel causes the feed spiroid to rotate and the reactant to move through the tubing.

43. The reactor of claim 41 wherein the spiroid is configured to sequentially transfer liquid phase and gas phase when the spiroid is rotated.

44. A bioreactor spiroid for sequentially transferring liquid phase and gas phase, the spiroid having (1) successive coils made of tubing, one of the coils being an inlet coil and another coil being a discharge coil with each coil having a volume less than the volume of the successive coil disposed closer to the inlet coil, and (2) an inlet in the inlet coil, the minimum number of coils (N) for a spiroid having a minimum total liquid head ($H_t$), assuming that the change in head ($\Delta h$) between each successive coil is held uniform, being determined by:

$$2(R_1-r)=Q((2H_t)/(N+1)),$$

where $R_1$ is the radius of the centerline of the tubing of the inlet coil, r is the inner radius of the tubing and Q is the reciprocal of the fraction of the approximate maximum head ($2(R_1-r)$) the discharge coil can reach when the spiroid is balanced with respect to hydrostatic and pneumatic pressures, the spiroid being configured so that rotation of the spiroid sequentially transfers liquid phase and gas phase and also generates an increase in pressure from the inlet coil to the discharge coil.

45. The spiroid of claim 44 wherein the spiroid is configured so that the liquid head in a given coil is the sum of the liquid head of the given coil and all previous coils starting with the inlet coil, and the spiroid is made of tubing of such cross-sectional dimension that bubbling through liquid entrapped in the tubing does not occur.

46. The spiroid of claim 44 wherein the tubing has such a small bore size that gas cannot escape through or around a liquid piston therein.

47. A method of transferring liquid phase and gas phase into a reactor comprising the steps of:

a. rotating a spiroid having (1) successive coils made of tubing, one of the coils being an inlet coil and another coil being a discharge coil, with each coil having a volume less than the volume of the successive coil disposed closer to the inlet coil, and (2) an inlet in the inlet coil, the minimum number of coils (N) for the spiroid having a minimum total liquid head ($H_t$), assuming that the change in head ($\Delta h$) between each successive coil is held uniform, being determined by:

$$2(R_1-r)=Q((2H_t)/(N+1)),$$

where $R_1$ is the radius of the centerline of the tubing of the discharge coil, r is the inner radius of the tubing and Q is the reciprocal of the fraction of the approximate maximum head ($2(R_1-r)$) the discharge coil can reach when the spiroid is balanced with respect to hydrostatic and pneumatic pressures; and b. transferring a liquid phase and gas phase through the spiroid.

* * * * *